United States Patent
O'Neill et al.

(10) Patent No.: US 10,240,094 B2
(45) Date of Patent: Mar. 26, 2019

(54) CONVERSION OF OXYGENATES TO HYDROCARBONS WITH VARIABLE CATALYST COMPOSITION

(71) Applicant: ExxonMobil Research and Engineering Company, Annandale, NJ (US)

(72) Inventors: Brandon J. O'Neill, Lebanon, NJ (US); Stephen J. McCarthy, Center Valley, PA (US); Mark A. Deimund, Jersey City, NJ (US); Ajit B. Dandekar, The Woodlands, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/862,977

(22) Filed: Jan. 5, 2018

(65) Prior Publication Data

US 2018/0201843 A1    Jul. 19, 2018

Related U.S. Application Data

(60) Provisional application No. 62/448,057, filed on Jan. 19, 2017.

(51) Int. Cl.

| | |
|---|---|
| *C07C 1/20* | (2006.01) |
| *C10G 3/00* | (2006.01) |
| *B01J 29/40* | (2006.01) |
| *B01J 29/70* | (2006.01) |
| *B01J 27/14* | (2006.01) |
| *B01J 29/06* | (2006.01) |
| *B01J 35/10* | (2006.01) |

(Continued)

(52) U.S. Cl.
CPC ............... *C10G 3/49* (2013.01); *B01J 27/14* (2013.01); *B01J 29/06* (2013.01); *B01J 29/405* (2013.01);

(Continued)

(58) Field of Classification Search
CPC .. C07C 1/20; C07C 1/22; C07C 1/207; C07C 1/24; C07C 1/26; C07C 1/322;

(Continued)

(56) References Cited

U.S. PATENT DOCUMENTS

| | | |
|---|---|---|
| 3,354,078 A | 11/1967 | Miale et al. |
| 3,702,886 A | 11/1972 | Argauer et al. |

(Continued)

OTHER PUBLICATIONS

The International Search Report and Written Opinion of PCT/US2018/012502 dated Apr. 24, 2018.

(Continued)

*Primary Examiner* — Sharon Pregler
(74) *Attorney, Agent, or Firm* — Liza Negron; Chad A. Guice

(57) ABSTRACT

Systems and methods are provided for modifying the composition of the conversion catalyst in a reactor for oxygenate conversion during conversion of an oxygenate feed to allow for adjustment of the slate of conversion products. The modification of the conversion catalyst can be performed by introducing a substantial portion (relative to the amount of catalyst inventory in the reaction system) of make-up catalyst having a distinct composition relative to the conversion catalyst in the reaction system. Introducing the distinct composition of make-up catalyst can modify the composition of the conversion catalyst in the reactor to allow for changes in the resulting product slate. By introducing the distinct catalyst composition, the conversion catalyst in the reactor can correspond to a different composition of catalyst than the overall average catalyst composition within the catalyst inventory in the reaction system.

23 Claims, 9 Drawing Sheets

(51) Int. Cl.
    *B01J 8/08*        (2006.01)
    *C07C 1/12*        (2006.01)
    *B01J 8/02*        (2006.01)
(52) U.S. Cl.
    CPC ......... *B01J 29/703* (2013.01); *B01J 29/7042*
        (2013.01); *B01J 29/7046* (2013.01); ***B01J
        35/10* (2013.01); *C10G 3/57* (2013.01); *C10G
        3/62*** (2013.01); *B01J 8/02* (2013.01); *B01J
        8/08* (2013.01); *C07C 1/12* (2013.01); *C10G
        2400/30* (2013.01)
(58) Field of Classification Search
    CPC .. C07C 1/323; B01J 27/14; B01J 29/06; B01J
        29/405; B01J 29/703; B01J 29/7042;
        B01J 29/7046; B01J 35/10; B01J 8/02;
        B01J 8/08; C10G 2400/30; C10G 3/49;
        C10G 3/57; C10G 3/62
    See application file for complete search history.

(56) References Cited

U.S. PATENT DOCUMENTS

| | | | |
|---|---|---|---|
| 3,709,979 A | 1/1973 | Chu | |
| 3,894,104 A | 7/1975 | Chang et al. | |
| RE29,948 E | 3/1979 | Dwyer et al. | |
| 4,582,815 A | 4/1986 | Bowes | |
| 9,090,525 B2 | 7/2015 | Brown | |
| 9,783,460 B2* | 10/2017 | Ou | C07C 1/22 |
| 2004/0104149 A1* | 6/2004 | Lomas | B01J 8/0055 |
| | | | 208/146 |
| 2005/0245781 A1 | 11/2005 | Martens et al. | |
| 2007/0037692 A1 | 2/2007 | Beech et al. | |
| 2013/0281753 A1 | 10/2013 | McCarthy et al. | |
| 2015/0174561 A1 | 6/2015 | McCarthy et al. | |
| 2015/0174562 A1 | 6/2015 | McCarthy et al. | |
| 2015/0174563 A1 | 6/2015 | McCarthy et al. | |

OTHER PUBLICATIONS

Weisz et al., "Superactive Crystalline Aluminosilicate Hydrocarbon Catalysts", Journal of Catalysis 4, 527-529 (1965).
Miale et al., "Catalysis by Crystalline Aluminosilicates", Journal of Catalysis 6, 278-287 (1966).
Olson et al., "Chemical and Physical Properties of the ZSM-5 Substitutional Series", Journal of Catalysis 61, 390-396 (1980).
Ghosh et al., "Development of a Detailed Gasoline Composition-Based Octane Model", Ind. Eng. Chem. Res. 2006, 45, 337-345.

* cited by examiner

CONVERSION OF OXYGENATES TO HYDROCARBONS WITH VARIABLE CATALYST COMPOSITION

CROSS-REFERENCE TO RELATED APPLICATIONS

This application claims the benefit of U.S. Provisional Application No. 62/448,057, filed on Jan. 19, 2017, the entire contents of which are incorporated herein by reference.

FIELD

This invention relates to integrated processes for forming aromatics and/or olefins by conversion of oxygenates.

BACKGROUND

A variety of industrial processes are known for conversion of low boiling carbon-containing compounds to higher value products. For example, methanol to gasoline (MTG) is a commercial process that produces gasoline from methanol using ZSM-5 catalysts. In the MTG process, methanol is first dehydrated to dimethyl ether. The methanol and/or dimethyl ether then react in a series of reactions that result in formation of aromatic, paraffinic, and olefinic compounds. The resulting product consists of liquefied petroleum gas (LPG) and a high-quality gasoline comprised of aromatics, paraffins, and olefins. The typical MTG hydrocarbon product consists of about 40-50% aromatics plus olefins and about 50-60% paraffins.

U.S. Pat. No. 3,894,104 describes a method for converting oxygenates to aromatics using zeolite catalysts impregnated with a transition metal. Yields of aromatics relative to the total hydrocarbon product are reported to be as high as about 58% with a corresponding total $C_5$+ yield as high as about 73%.

U.S. Patent Application Publication 2013/0281753 describes a phosphorous modified zeolite catalyst. The phosphorous modification reduces the change in alpha value for the catalyst after the catalyst is exposed to an environment containing steam. The phosphorous modified catalysts are described as being suitable, for example, for conversion of methanol to gasoline boiling range compounds.

U.S. Patent Application Publications 2015/0174561, 2015/0174562, and 2015/0174563 describe catalysts for conversion of oxygenates to aromatics. The catalysts include a zeolite, such as an MFI or MEL framework structure zeolite, with a supported Group 12 metal on the catalyst.

U.S. Pat. No. 9,090,525 describes conversion of oxygenates in the presence of a zeolitic catalyst to form naphtha boiling range compounds with increased octane. A portion of the naphtha boiling range olefins from an initial conversion product are recycled to the oxygenate conversion process to allow for formation of heavier naphtha boiling range compounds, including aromatics.

SUMMARY

In some aspects, a method for forming a hydrocarbon composition is provided. The method can include introducing catalyst particles comprising a first catalyst system at a first catalyst addition rate per day into a reaction system comprising a reactor. The reaction system can further comprise an inventory volume of catalyst particles of a second catalyst system, a composition of the second catalyst system being distinct from a composition of the first catalyst system by at least 5 wt %. The first catalyst addition rate per day can comprise at least about 5 vol % of the inventory volume. A feed comprising oxygenates can be exposed to conversion catalyst in the reactor at conversion conditions to form a converted effluent comprising a hydrocarbon fraction, the conversion catalyst comprising at least a portion of the first catalyst system and at least a portion of the second catalyst system. The conversion catalyst can optionally comprise at least a first catalyst and a second catalyst. The reactor can optionally comprise a fluidized bed reactor, a moving bed reactor, a riser reactor, or a combination thereof.

In some aspects, the conversion catalyst in the reactor can comprise the first catalyst having a first average catalyst exposure time and the second catalyst having a second average catalyst exposure time, a selectivity of the first catalyst for aromatics at the conversion conditions being at least 10 wt % greater than a selectivity of the second catalyst for aromatics at the conversion conditions.

In some aspects, the second catalyst system can comprise the first catalyst and the second catalyst, the method further comprising regenerating at least a portion of the conversion catalyst exposed to the feed comprising oxygenates, the regenerated second catalyst comprising at least 0.1 wt % of coke, or 0.1 wt % to 10 wt % of coke, or 1.0 wt % to 25 wt % of coke, the regenerated first catalyst optionally comprising 0.1 wt % or less of coke.

In various aspects, at least one of the first catalyst system and the second catalyst system can comprise: i) at least 10 wt % of catalyst particles comprising a zeolite having MFI framework structure, the zeolite having a silicon to aluminum ratio of 10 to 200 and an Alpha value of at least 5; ii) at least 10 wt % of catalyst particles comprising a zeolite having MRE framework structure, the zeolite having a silicon to aluminum ratio of 10 to 100 and an Alpha value of at least 5, the first catalyst system and/or second catalyst system optionally further comprising 0.1 wt % to 3.0 wt % of a transition metal supported on the catalyst particles comprising the zeolite having MRE framework structure; iii) at least 10 wt % of catalyst particles comprising a zeolite having MRE framework structure, MTW framework structure, TON framework structure, MTT framework structure, MFS framework structure or a combination thereof; and/or iv) at least 10 wt % of catalyst particles comprising a zeolite having a largest pore channel size corresponding to an 8-member ring. Optionally, the at least 10 wt % of catalyst particles can further comprise 0.1 wt % to 3.0 wt % of a transition metal supported on the catalyst particles, the 0.1 wt % to 3.0 wt % of transition metal optionally comprising 0.1 wt % to 3.0 wt % of Zn. Optionally, the conversion catalyst can further comprise phosphorus supported on the conversion catalyst.

In some aspects, the method can further include a) wherein the oxygenates comprise methanol, the conversion catalyst comprising an average catalyst exposure time of 1 grams to 2000 grams of oxygenate per gram of catalyst; or b) wherein the average catalyst exposure time of the second catalyst is 50 grams to 180 grams of methanol per gram of catalyst; or c) an average catalyst exposure time of the first catalyst being different from an average catalyst exposure time of the second catalyst; or d) a combination thereof of a), b) and/or c).

In some aspects, the first catalyst addition rate per day can comprise at least about 10 vol % of the inventory volume, or at least 20 vol %; or the composition of the second catalyst system can differ from the composition of the first catalyst system by at least 10 wt %, or at least 30 wt %, or at least 50 wt %, or at least 70 wt %; or a combination thereof. In some aspects, the hydrocarbon fraction can comprise olefins, or the hydrocarbon fraction can comprises a naphtha boiling range fraction, or a combination thereof.

In various aspects, a system for conversion of oxygenates to hydrocarbons is provided. The system can include a first catalyst store comprising a first catalyst comprising a first zeolite framework structure; a second catalyst store comprising a second catalyst, the second catalyst comprising a second zeolite framework structure different from the first zeolite framework structure; and a reaction system comprising a reactor, a regenerator, and a reaction system internal catalyst store. The first catalyst store and the second catalyst store can be in fluid communication with the reaction system. The reaction system can further comprise an inventory volume of catalyst particles, the catalyst particles comprising the first catalyst and the second catalyst. The first catalyst in the internal catalyst store can comprising less than 0.1 wt % coke and/or the second catalyst in the internal catalyst store can comprise greater than 0.1 wt % coke. In an aspect, the reactor volume of the reactor can comprise the first catalyst, the second catalyst, and methanol.

In some aspects, the first catalyst can comprise a zeolite having MFI framework structure, the zeolite having a silicon to aluminum ratio of 10 to 200 and an Alpha value of at least 5, the first catalyst optionally further comprising 0.1 wt % to 3.0 wt % of a transition metal supported on the catalyst. In some aspects, the second catalyst can comprise a zeolite having MRE framework structure, the zeolite having a silicon to aluminum ratio of 10 to 100 and an Alpha value of at least 5, the second catalyst optionally further comprising 0.1 wt % to 3.0 wt % of a transition metal supported on the catalyst; or a combination thereof. In some aspects, at least one of the first catalyst and the second catalyst can comprise a zeolite having a largest pore channel size corresponding to an 8-member ring.

DETAILED DESCRIPTION

Figure 1:
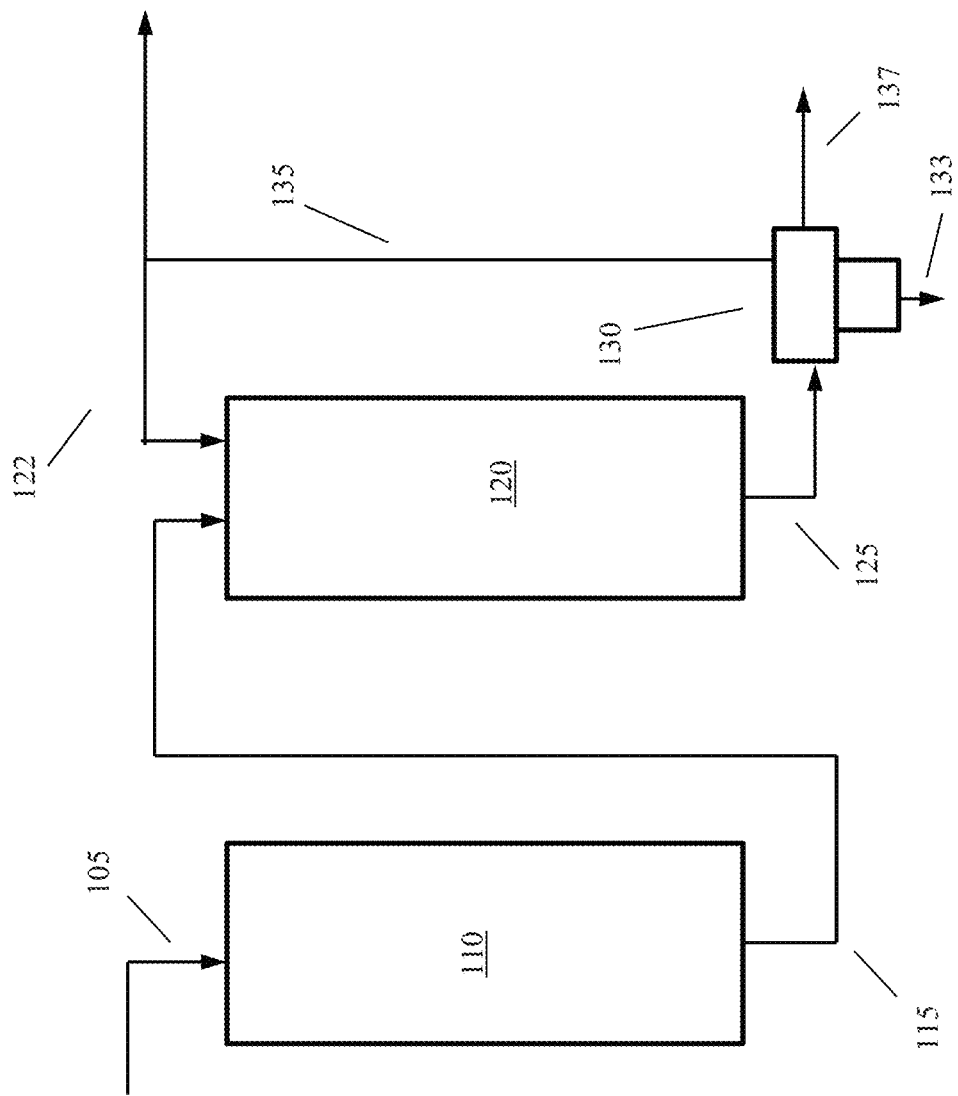
FIG. 1 schematically shows an example of a reaction system including a conversion reactor.

In various aspects, systems and methods are provided for modifying the composition of the conversion catalyst in a reactor for oxygenate conversion during conversion of an oxygenate feed to allow for adjustment of the slate of conversion products. The modification of the conversion catalyst can be performed by introducing a substantial portion (relative to the amount of catalyst inventory in the reaction system) of make-up catalyst having a distinct composition relative to the conversion catalyst in the reaction system. Introducing the distinct composition of make-up catalyst can modify the composition of the conversion catalyst in the reactor to allow for changes in the resulting product slate. For example, if the conversion catalyst in a reaction system has a high selectivity for aromatics, a distinct catalyst system with an increased selectivity for olefins and/or reduced selectivity for aromatics can be introduced as make-up catalyst to allow for changes in the products in the conversion effluent. By introducing the distinct catalyst composition, the conversion catalyst in the reactor can correspond to a different composition of catalyst than the overall average catalyst composition within the catalyst inventory in the reaction system. If the distinct composition is introduced into the reaction system for a sufficient period of time, the catalyst composition within the reaction system can eventually converge toward the composition being introduced into the reaction system.

Natural gas, coal, and/or biomass are becoming increasingly important sources of carbon for use in production of fuel and/or lubricant products. A first step in conversion of carbon from a natural gas, coal, and/or biomass source can be a conversion of methane to methanol. Once methanol is formed, various fixed bed, fluid bed, and moving bed processes can be used to convert methanol to higher value products, such as fuels, aromatics, and/or olefins. Such processes can use zeolitic catalysts, such as MFI framework (ZSM-5) zeolitic catalysts. Optionally, the zeolitic catalysts can include a supported transition metal, such as Zn, to provide increased selectivity for a desired product, such as aromatics.

Some difficulties with conversion of methanol to naphtha boiling range products (such as aromatics) for use as gasoline can be related to the tendency for the zeolitic catalyst to deactivate relatively quickly. Even relatively small exposures of feed to a zeolitic catalyst can result in loss of aromatic selectivity, with a corresponding increase in formation of lower value paraffins. For zeolitic frameworks other than MFI, the catalyst deactivation can also impact the general ability of the catalyst to convert oxygenates within a feed.

Another challenge with oxygenate conversion can be related to producing a desired product slate in the conversion effluent. For example, the desired type of products from an oxygenate conversion reaction, such as light olefins ($C_2$-$C_3$), heavy olefins (primarily $C_{3+}$), or aromatics can change rapidly depending on market conditions. Instead of having multiple reaction systems tailored to emphasize production of each type of product, the systems and methods described herein can allow a single reaction system to be operated to allow for tailoring of the product slate. This can include changing the reactor operating conditions, changing the regeneration amount of the conversion catalyst, and/or modifying the composition of the conversion catalyst.

In this discussion, the catalyst inventory of a reaction system is defined to include all catalyst particles within processing volume of the reaction system. Thus, the catalyst inventory is defined to include catalyst in a reactor, catalyst in a regenerator, any internal catalyst store for holding catalyst after regeneration and prior to introduction into the reactor, and any catalyst in pipes or conduits for transport between the reactor, regenerator, and/or internal catalyst store. Under this definition, catalyst in a make-up catalyst store (or other external catalyst store) is excluded from the catalyst inventory, until such time that the catalyst from the external catalyst store is moved into the processing volume of the reaction system. The catalyst inventory of a catalyst system can typically be at least 110 wt % of the amount of catalyst in the reactor during operation, such as 110 wt % to 200 wt %, or 110 wt % to 400 wt %, or any other convenient amount of catalyst.

In this discussion, a catalyst system is defined as the average catalyst composition, excluding any coke on catalyst particles, within a defined volume in a reaction system. As an example, a reaction system including multiple catalyst stores of make-up catalyst can include a plurality of catalyst systems. A first catalyst system can correspond to the existing catalyst composition within the processing volume (i.e., the catalyst inventory) of the reaction system. A second catalyst system can correspond to the composition of the conversion catalyst currently within the reactor. A third catalyst system can correspond to catalyst in an external catalyst store. Optionally, multiple different catalyst systems can be held in external catalyst stores to increase the potential flexibility for modifying the catalyst composition in the processing volume and/or the reactor. It is noted that because the amount of coke on catalyst particles is not considered when defining a catalyst system, the regeneration state of catalyst particles does not alter the nature of a catalyst system.

In this discussion, octane rating is defined as (RON+MON)/2, where RON is research octane number and MON is motor octane number. For values reported in the examples below, RON and MON values were determined based on a published model that determines octane ratings for a blend of components based to determine a blended octane. The model is described at Ind Eng Chem Res 2006, 45, 337-345. The model is believed to correlate with experimentally determined values. In the claims below, Research Octane Number (RON) is determined according to ASTM D2699. Motor Octane Number (MON) is determined according to ASTM D2700.

In this discussion, the naphtha boiling range is defined as 50° F. (~10° C., roughly corresponding to the lowest boiling point of a pentane isomer) to 350° F. (177° C.). The distillate fuel boiling range, is defined as 350° F. (177° C.) to 700° F. (371° C.). Compounds ($C_{4-}$) with a boiling point below the naphtha boiling range can be referred to as light ends. It is noted that due to practical consideration during fractionation (or other boiling point based separation) of hydrocarbon-like fractions, a fuel fraction formed according to the methods described herein may have T5 and T95 distillation points corresponding to the above values (or T10 and T90 distillation points), as opposed to having initial/final boiling points corresponding to the above values. While various methods are available for determining boiling point information for a given sample, for the claims below ASTM D86 is a suitable method for determining distillation points (including fractional weight distillation points) for a composition.

Distinct Catalyst Systems

In this discussion, the difference between two catalyst systems can be characterized based on the total weight of catalyst particles within each catalyst system, with catalyst systems that differ by at least 5 wt % being considered distinct (i.e., not the same catalyst system), or at least 10 wt %, or at least 20 wt %, or at least 40 wt %. The percentage of catalyst particles having a particular type of zeolite (including heteroatoms in the zeolite framework), binder, and supported metals can then be compared. Two types of catalyst can be considered similar when the catalysts are a) composed of the same type of zeolite framework, b) have a molar ratio of silicon atoms to aluminum atoms in the zeolite framework that differs by less than 10, c) include an amount of binder that differs by less than 10 wt % relative to the weight of the catalyst particles, d) have the same types of supported metals, to within 0.1 wt % for each type of supported metal.

To illustrate the determination of whether two catalyst systems are the same or different, several examples of catalyst systems can be provided. As a simple example, a first catalyst system can correspond to 1.0 wt % Zn on self-bound ZSM-5, while a second catalyst system can correspond to 1.0 wt % Zn on self-bound ZSM-48. Without knowing the silicon to aluminum ratios of the zeolites, the presence of different framework structures means that the catalyst systems are different.

As a second example, a first catalyst system can correspond to 46 wt % of 1.0 wt % Zn on self-bound ZSM-5 (silicon to aluminum ratio of 30) and 54 wt % of 1.0 wt % Zn on self-bound ZSM-48 (silicon to aluminum ratio of 75). A second catalyst system can correspond to the same two types of catalyst, but in a 50 wt %/50 wt % mixture. In this second example, the difference in the amount of ZSM-5 catalyst between the first catalyst system and second catalyst system is 4 wt %. The difference in the amount of ZSM-48 catalyst between the first catalyst system and the second catalyst system is also 4 wt %. This corresponds to a net difference of 8 wt % between the two catalyst systems. Based on the definition above, at least 10 wt % of two catalyst systems needs to correspond to different types of catalyst particles for the catalyst systems to be considered distinct. Thus, in this second example, the first catalyst system and second catalyst system are not considered distinct.

In a third example, a first catalyst system can correspond to 46 wt % of 1.0 wt % Zn on self-bound ZSM-5 (silicon to aluminum ratio of 30) and 54 wt % of 1.0 wt % Zn on self-bound ZSM-48 (silicon to aluminum ratio of 75). A second catalyst system can correspond to 46 wt % of 1.0 wt % Zn plus 0.05 wt % P on self-bound ZSM-5 (silicon to aluminum ratio of 25) and 54 wt % of 1.0 wt % Zn on self-bound ZSM-48 (silicon to aluminum ratio of 75). In this example, the catalyst systems are not considered distinct. In this example, the ZSM-48 catalyst particles in the two catalyst systems are the same. Although the ZSM-5 catalyst particles have some differences, the differences are not substantial enough to consider the catalyst systems distinct. In particular, the amount of phosphorus on the ZSM-5 in the second catalyst system is less than 0.1 wt %, so that does not cause the catalysts to be distinct under the definition provided herein. Additionally, the difference between the silicon to aluminum ratio for the ZSM-5 in the two catalyst systems is only 5 (30 versus 25), which also does not correspond to distinct catalyst under the definition herein.

In a fourth example, a first catalyst system can correspond to 46 wt % of 1.0 wt % Zn on self-bound ZSM-5 (silicon to aluminum ratio of 30) and 54 wt % of 1.0 wt % Zn on self-bound ZSM-48 (silicon to aluminum ratio of 75). A second catalyst system can correspond to 46 wt % of 1.0 wt % Zn plus 0.05 wt % P on self-bound ZSM-5 (silicon to aluminum ratio of 30) and 54 wt % of 1.5 wt % Zn on self-bound ZSM-48 (silicon to aluminum ratio of 90). In this example, the catalyst systems are distinct based on the differences between the ZSM-48 catalysts, as both the Zn content and the silicon to aluminum ratio differ by enough for the ZSM-48 catalysts to be considered distinct.

Modification of the Composition of Conversion Catalyst

As further described below, a variety of zeolitic catalysts can be suitable for conversion of methanol and/or other oxygenates to naphtha boiling range products and/or olefins. The nature of the products from the conversion reaction can be modified in part based on the composition of the conversion catalyst that is exposed to the feed. In various aspects, the composition of the conversion catalyst can be modified (relative to the composition of the catalyst inventory in the reaction system) by introduction of a different catalyst system at a substantial addition rate.

Conventionally, fresh (or other) make-up catalyst is typically added to a reaction system at a relatively low rate. Relative to the catalyst inventory in a reaction system, the make-up rate of catalyst on a daily basis can typically be about 1 wt % or less of the catalyst inventory in a reaction system. By contrast, in various aspects the rate of catalyst addition per day of a distinct catalyst system to a reaction system can be at least 5 wt % of the catalyst inventory of the reaction system, or at least 10 wt %, or at least 20 wt %, such as up to about 50 wt % or more. This can allow the composition of the catalyst system in a reaction system to be modified to correspond to a new catalyst system (such as no longer being distinct from a new catalyst system being added to the reaction system) in about a month or less of processing time. During this change in the composition of the catalyst in the reaction system, the reaction system can continue to process feed and/or otherwise continue operation.

A second catalyst system that is distinct from the (initial or existing) catalyst system in a reaction system catalyst inventory can be selected, for example, based on differing reactivity of the two catalyst systems. For example, the existing catalyst system in a reactor may correspond to a catalyst system with high selectivity for aromatics, such as transition metal-enhanced MFI framework catalyst. A second catalyst system can correspond to a catalyst system with high selectivity for aromatics, such as an MRE framework catalyst. In some aspects, the difference in aromatic selectivity for a first catalyst system and a second catalyst system can be at least about 5 wt % relative to the total hydrocarbon product that would be generated by each catalyst system at the reaction conditions, or at least 10 wt %. Additionally or alternately, the difference in olefin selectivity for a first catalyst system and a second catalyst system can be at least about 5 wt % relative to the total hydrocarbon product that would be generated by each catalyst system at the reaction conditions, or at least 10 wt %. Additionally or alternately, the difference in small olefin selectivity ($C_2$ and $C_3$ olefins) for a first catalyst system and a second catalyst system can be at least about 5 wt % relative to the total hydrocarbon product that would be generated by each catalyst system at the reaction conditions, or at least 10 wt %. Additionally or alternately, the difference in large olefin selectivity ($C_{3+}$ olefins) for a first catalyst system and a second catalyst system can be at least about 5 wt % relative to the total hydrocarbon product that would be generated by each catalyst system at the reaction conditions, or at least 10 wt %.

In addition to modifying the composition of catalyst within a reaction system, the amount of regeneration performed on catalyst within the reaction system can also be used to modify catalyst activity and/or selectivity. In aspects where the catalyst system within a reaction system comprises at least two types of catalysts, the regeneration rate of each type of catalyst may be different. In some aspects, the regeneration conditions can be selected to provide complete regeneration of both types of catalysts (or all types of catalysts, if three or more types are present). In other aspects, the regeneration conditions can be selected to provide complete regeneration of a first catalyst, while a second catalyst undergoes only partial regeneration. In still other aspects, the regeneration conditions can result in only partial regeneration of both catalysts. As further defined below, partial regeneration of at least one catalyst in a catalyst system can cause the average catalyst exposure time to be different for the catalysts within the catalyst inventory of a reaction system.

Feedstocks and Products—Oxygenate Conversion

In various aspects, catalysts described herein can be used for conversion of oxygenate feeds to aromatics and/or olefins products, such as oxygenates containing at least one $C_1$-$C_4$ alkyl group and/or other oxygenates. Examples of suitable oxygenates include feeds containing methanol, dimethyl ether, $C_1$-$C_4$ alcohols, ethers with $C_1$-$C_4$ alkyl chains, including both asymmetric ethers containing $C_1$-$C_4$ alkyl chains (such as methyl ethyl ether, propyl butyl ether, or methyl propyl ether) and symmetric ethers (such as diethyl ether, dipropyl ether, or dibutyl ether), or combinations thereof. It is noted that oxygenates containing at least one $C_1$-$C_4$ alkyl group are intended to explicitly identify oxygenates having alkyl groups containing about 4 carbons or less. Preferably the oxygenate feed can include at least about 30 wt % of one or more suitable oxygenates, or at least about 50 wt %, or at least about 75 wt %, or at least about 90 wt %, or at least about 95 wt %. Additionally or alternately, the oxygenate feed can include at least about 50 wt % methanol, such as at least about 75 wt % methanol, or at least about 90 wt % methanol, or at least about 95 wt % methanol. In particular, the oxygenate feed can include 30 wt % to 100 wt % of oxygenate (or methanol), or 50 wt % to 95 wt %, or 75 wt % to 100 wt %, or 75 wt % to 95 wt %. The oxygenate feed can be derived from any convenient source. For example, the oxygenate feed can be formed by reforming of hydrocarbons in a natural gas feed to form synthesis gas ($H_2$, CO, $CO_2$), and then using the synthesis gas to form methanol (or other alcohols). As another example, a suitable oxygenate feed can include methanol, dimethyl ether, or a combination thereof as the oxygenate.

In addition to oxygenates, a feed can also include diluents, such as water (in the form of steam), nitrogen or other inert gases, and/or paraffins or other non-reactive hydrocarbons. In some aspects, the source of olefins can correspond to a low purity source of olefins, so that the source of olefins corresponds to 20 wt % or less of olefins. In some aspects, the portion of the feed corresponding to components different from oxygenates and olefins can correspond to 1 wt % to 60 wt % of the feed, or 1 wt % to 25 wt %, or about 10 wt % to about 30 wt %, or about 20 wt % to about 60 wt %. Optionally, the feed can substantially correspond to oxygenates and olefins, so that the content of components different from oxygenates and olefins is 1 wt % or less (such as down to 0 wt %).

In some aspects, such as aspects related to oxygenate conversion using an MFI or MEL framework catalyst, the yield of aromatics relative to the total hydrocarbon product can be about 35 wt % to about 60 wt %, or about 38 wt % to about 60 wt %, or about 40 wt % to about 52 wt %, or about 38 wt % to about 45 wt %. For example, the yield of aromatics relative to the total hydrocarbon product can be at least about 35 wt %, or at least about 38 wt %, or at least about 40 wt %, or at least about 45 wt %. Additionally or alternately, the yield of aromatics relative to the total hydrocarbon product can be about 60 wt % or less, or about 55 wt % or less, or about 52 wt % or less, or about 50 wt % or less. In various aspects, the yield of olefins relative to the total hydrocarbon product can be about 2.0 wt % to about 30 wt %, or about 2.0 wt % to 25 wt %, or about 5.0 wt % to about 20 wt %, or about 10 wt % to about 20 wt %. For example, the yield of olefins relative to the total hydrocarbon product can be at least about 2.0 wt %, or at least about 5.0 wt %, or at least about 10 wt %. Additionally or alternately, the yield of olefins relative to the total hydrocarbon product can be about 30 wt % or less, or about 25 wt % or less, or about 20 wt % or less. In various aspects, the yield of paraffins relative to the total hydrocarbon product can be about 20 wt % to about 45 wt %, or about 20 wt % to about 35 wt %, or about 25 wt % to about 45 wt %, or about 25 wt % to about 40 wt %. For example, the yield of paraffins relative to the total hydrocarbon product can be at least about 20 wt %, or at least about 25 wt %, or at least about 30 wt % and/or the yield of paraffins relative to the total hydrocarbon product can be about 45 wt % or less, or about 40 wt % or less, or about 35 wt % or less. In the claims below, the relative amounts of paraffins, olefins, and aromatics in a sample can be determined based on ASTM D6839. For the paraffins and olefins generated during oxygenate conversion, at least 50 wt % of the olefins can correspond to $C_3$ and $C_4$ olefins and/or at least 50 wt % of the paraffins can correspond to $C_3$ and $C_4$ paraffins. Additionally or alternately, less than 10 wt % of the paraffins can correspond to $C_1$ paraffins (methane).

In some aspects, such as aspects related to oxygenate conversion using an MRE framework catalyst, the yield of aromatics relative to the total hydrocarbon product can be about 5 wt % to about 30 wt %, or about 10 wt % to about 30 wt %, or about 10 wt % to about 25 wt %, or about 5 wt % to about 20 wt %. For example, the yield of aromatics relative to the total hydrocarbon product can be at least about 5 wt %, or at least about 10 wt %, or at least about 15 wt %. Additionally or alternately, the yield of aromatics relative to the total hydrocarbon product can be about 30 wt % or less, or about 25 wt % or less, or about 20 wt % or less. In various aspects, the yield of olefins relative to the total hydrocarbon product can be about 20 wt % to about 60 wt %, or about 25 wt % to 60 wt %, or about 20 wt % to about 40 wt %, or about 25 wt % to about 50 wt %. For example, the yield of olefins relative to the total hydrocarbon product can be at least about 20 wt %, or at least about 25 wt %, or at least about 30 wt %. Additionally or alternately, the yield of olefins relative to the total hydrocarbon product can be about 60 wt % or less, or about 50 wt % or less, or about 40 wt % or less. In various aspects, the yield of paraffins relative to the total hydrocarbon product can be about 20 wt % to about 50 wt %, or about 20 wt % to about 35 wt %, or about 25 wt % to about 45 wt %, or about 25 wt % to about 40 wt %. For example, the yield of paraffins relative to the total hydrocarbon product can be at least about 20 wt %, or at least about 25 wt %, or at least about 30 wt % and/or the yield of paraffins relative to the total hydrocarbon product can be about 50 wt % or less, or about 45 wt % or less, or about 40 wt % or less, or about 35 wt % or less. For the paraffins and olefins generated during oxygenate conversion, at least 50 wt % of the olefins can correspond to $C_3$ and $C_4$ olefins and/or at least 50 wt % of the paraffins can correspond to $C_3$ and $C_4$ paraffins. Additionally or alternately, less than 10 wt % of the paraffins can correspond to $C_1$ paraffins (methane).

The total hydrocarbon product in the conversion effluent can include a naphtha boiling range portion, a distillate fuel boiling range portion, and a light ends portion. Optionally but preferably, the conversion effluent can include less than 1.0 wt % of compounds boiling above the distillate fuel boiling range (371° C.+), such as having a final boiling point of 371° C. or less. In various aspects, the selectivity for forming/yield of a naphtha boiling range portion can be at least about 35 wt % and/or about 75 wt % or less. For example, the selectivity for forming/yield of a naphtha boiling range portion can be about 35 wt % to 75 wt %, or 40 wt % to 65 wt %, or 40 wt % to 60 wt %, or 45 wt % to 70 wt %.

The naphtha boiling range portion formed from a conversion process can have an octane rating of at least 80, or at least 90, or at least 95, or at least 97, or at least 100, or at least 102, or at least 105, such as up to 110. In particular, in aspects involving an MFI or MEL framework catalyst, the octane rating can be 80 to 110, or 95 to 110, or 97 to 110, or 100 to 110. Additionally or alternately, in aspects involving a MRE framework catalyst, the octane rating can be 80 to 97 or 90 to 97. As defined above, the octane rating is corresponds to (RON+MON)/2).

The conversion conditions can also result in generation of CO and/or $CO_2$. In some aspects, the amount of combined CO, $CO_2$, and $CH_4$ can correspond to about 6.0 wt % or less of the total hydrocarbon product in a conversion effluent, or about 5.0 wt % or less. In this discussion and the claims below, the amounts of CO and $CO_2$ in a conversion effluent are included when determining the amount of the total hydrocarbon product (such as the weight of the total hydrocarbon product).

Suitable and/or effective conditions for performing a conversion reaction can include average reaction temperatures of about 300° C. to about 550° C. (or about 350° C. to about 550° C., or about 400° C. to about 500° C.), total pressures between about 10 psig (~70 kPag) to about 400 psig (~2700 kPag), or about 50 psig (~350 kPag) to about 350 psig (~2400 kPag), or about 100 psig (~700 kPag) to about 300 psig (~2100 kPag), and an oxygenate space velocity between about 0.1 $h^{-1}$ to about 10 $h^{-1}$ based on weight of oxygenate relative to weight of catalyst. For example, the average reaction temperature can be at least about 300° C., or at least about 350° C., or at least about 400° C., or at least about 450° C. Additionally or alternately, the average reaction temperature can be about 550° C. or less, or about 500° C. or less, or about 450° C. or less, or about 400° C. or less. In this discussion, average reaction temperature is defined as the average of the temperature at the reactor inlet and the temperature at the reactor outlet for the reactor where the conversion reaction is performed. As another example, the total pressure can be at least about 70 kPag, or at least about 350 kPag, or at least about 500 kPag, or at least about 700 kPag, or at least about 1000 kPag. Additionally or alternately, the total pressure can be about 3000 kPag or less, or about 2700 kPag or less, or about 2400 kPag or less, or about 2100 kPag or less.

Optionally, a portion of the conversion effluent can be recycled for inclusion as part of the feed to the conversion reactor. For example, at least a portion of the light ends from the conversion effluent can be recycled as part of the feed. The recycled portion of the light ends can correspond to any convenient amount, such as 25 wt % to 75 wt % of the light ends. Recycling of light ends can provide olefins, which can serve as an additional reactant in the conversion reaction, as well as providing a mechanism for temperature control.

Various types of reactors can provide a suitable configuration for performing a conversion reaction. Suitable reactors can include moving bed reactors (such as riser reactors), and fluidized bed reactors. It is noted that the activity and/or selectivity of a catalyst for oxygenate conversion can vary as the catalyst is exposed to increasing amounts of oxygenate feed. This modification of the catalyst activity is believed to be due to the formation of coke on the catalyst.

The modification of the catalyst activity and/or selectivity with increasing average catalyst exposure time can be reversed at least in part by regenerating the catalyst. In some aspects, a full regeneration can be performed on a catalyst, so that the average amount of coke present on the regenerated catalyst is less than 0.1 wt %. In other aspects, a partial regeneration can be performed, so that the average amount of coke present on the regenerated catalyst after regeneration is greater than 0.1 wt %. The average amount of coke present on a catalyst sample can be readily determined by thermogravimetric analysis. During partial regeneration, the amount of coke on a regenerated catalyst can correspond to 0.1 wt % to 25 wt % relative to the weight of the catalyst. For example, the amount of coke on regenerated catalyst can be 0.1 wt % to 10 wt % relative to the weight of the catalyst, or 1.0 wt % to 25 wt %.

In aspects where a catalyst can be withdrawn from the reactor for regeneration and recycle during operation of the reactor, such as a moving bed reactor and/or fluidized bed reactor, catalyst can be withdrawn and replaced with make-up (fresh) and/or regenerated catalyst. It is noted that withdrawing catalyst from the reactor for regeneration is distinct from removing catalyst entirely from the reaction system and replacing the removed catalyst with fresh make-up catalyst. In this discussion, when full regeneration is performed on a catalyst (less than 0.1 wt % average coke remaining on the regenerated catalyst), the average catalyst exposure time for the regenerated catalyst is defined to be zero for purposes of determining average catalyst exposure time for catalyst within the reactor. In such aspects when full regeneration is being performed, the average catalyst exposure time for catalyst being exposed to oxygenate can be determined based on a) the flow rate of oxygenate into the reactor relative to the amount of catalyst in the reactor, and b) the average residence time of the catalyst in the reactor. These values can allow for a determination of the average grams of oxygenate per gram of catalyst in the reactor (i.e., the average catalyst exposure time).

In a moving bed reactor, the residence time for catalyst can correspond to the amount of time required for a catalyst particle to travel the length of the bed to the exit, based on the average velocity of the moving bed. As an example, the flow of methanol into a moving bed reactor can correspond to a space velocity of 1.0 $h^{-1}$, which means 1 g of methanol per g of catalyst per hour. In such an example, if the average residence time for catalyst in the reactor is 48 hours (based on the average velocity of the moving bed relative to the size of the bed), one of skill in the art would expect a distribution of catalyst exposure times within the reactor. The average catalyst exposure time for this distribution can roughly be approximated based on the average of a) the catalyst exposure time for new catalyst entering the reactor and b) the catalyst exposure time for catalyst exiting the reactor. For catalyst that is completely regenerated and/or fresh catalyst, the catalyst exposure time when entering the reactor is defined as 0. In this example, the catalyst exposure time existing the reactor is 48 g of methanol per g of catalyst. Thus, for this example, the average catalyst exposure time for catalyst in the moving bed would be 24 g of methanol per g of catalyst. This value also corresponds to the amount of catalyst exposure the catalyst receives during the residence time within the reactor. Similarly, in aspects involving a fluidized bed, the catalyst residence time can be determined based on the rate of removal of catalyst from the reactor for regeneration. The catalyst residence time can correspond to the amount of time required to remove an amount of catalyst that is equivalent to the weight of the catalyst bed. Based on that residence time, the average catalyst exposure time can be calculated in a similar manner to the calculation for a moving bed.

During a partial regeneration, a catalyst can be exposed to an oxidizing environment for removal of coke from the catalyst, but the net amount of coke remaining on the catalyst after partial regeneration can be greater than 0.1 wt %. When a partial regeneration is performed, the effective average catalyst exposure time for the catalyst after regeneration will be a value other than zero, due to the amount of remaining coke on the catalyst. When a partial regeneration is performed, the amount of coke removal can roughly scale in a linear manner with the effective average catalyst exposure time of the partially regenerated catalyst. In this discussion and the claims below, when a catalyst is partially regenerated, the average catalyst exposure time for the partially regenerated catalyst is determined by multiplying the average catalyst exposure time prior to regeneration by the wt % of coke remaining on the catalyst after partial regeneration. As an example, a hypothetical catalyst may have an exposure time of 100 g methanol per g catalyst prior to regeneration. In this example, partial regeneration is used to remove 60 wt % of the coke on the catalyst. This means that 40 wt % (or 0.4 expressed as a fraction) of the coke remains on the catalyst after regeneration. In such an example, the average catalyst exposure time for the regenerated catalyst would be 0.4×100=40 g methanol per g catalyst.

In aspects where partial regeneration is performed, the calculation for the average catalyst exposure time for catalyst in the reactor can be modified based to account for the fact that any recycled catalyst will have a non-zero initial value of catalyst exposure time. The same calculation described above can be used to determine an initial value. The non-zero catalyst exposure time for the regenerated catalyst can then be added to the initial value to determine the average catalyst exposure time within the reactor. In the example noted above, if the average catalyst exposure time for partially regenerated catalyst is 10 g methanol per g catalyst, and if the amount of average exposure within the reactor is 24 g methanol per g catalyst as calculated above, then the average catalyst exposure time for the system when using partial regeneration would be 34 g methanol per g catalyst. It is also noted that a portion of the catalyst introduced into a reactor may correspond to fresh make-up catalyst instead of partially regenerated catalyst. In such aspects, the catalyst exposure time for the catalyst introduced into the reactor can be a weighted average of the fresh make-up catalyst (zero exposure time) and the catalyst exposure time for the partially regenerated catalyst.

For a catalyst including an MFI framework zeolite, the catalyst recycle rate can be dependent on the desired products, with catalyst recycle rates that produce an average catalyst exposure time/average cycle length for catalyst in the reactor of about 1 g $CH_3OH$/g catalyst to about 2000 g $CH_3OH$/g catalyst potentially being suitable, or about 50 g $CH_3OH$/g catalyst to about 1000 g $CH_3OH$/g catalyst, or about 100 g $CH_3OH$/g catalyst to about 1500 g $CH_3OH$/g catalyst, or about 100 g $CH_3OH$/g catalyst to about 1000 g $CH_3OH$/g catalyst. The target average catalyst exposure time can be dependent on the specific nature of the catalyst and/or the desired product mix. In some aspects where shorter average catalyst exposure times are desired, the average catalyst exposure time can be about 1 g $CH_3OH$/g catalyst to about 200 g $CH_3OH$/g catalyst, or about 5 g $CH_3OH$/g catalyst to about 150 g $CH_3OH$/g catalyst, or about 1 g $CH_3OH$/g catalyst to about 100 g $CH_3OH$/g catalyst. In other aspects where longer times are desired, the average catalyst exposure time can be about 200 g $CH_3OH$/g catalyst to about 2000 g $CH_3OH$/g catalyst, or about 400 g $CH_3OH$/g catalyst to about 1500 g $CH_3OH$/g catalyst, or about 500 g $CH_3OH$/g catalyst to about 1000 g $CH_3OH$/g catalyst. The above average catalyst exposure times can be achieved, for example, by withdrawing about 0.01 wt % to about 3.0 wt % of catalyst per 1 g of methanol exposed to a g of conversion catalyst, or about 0.01 wt % to about 1.5 wt %, or about 0.1 wt % to about 3.0 wt %, or about 1.0 wt % to about 3.0 wt %. It is noted that these withdrawal rates could be modified, for example, if only a partial regeneration is performed on withdrawn catalyst. For catalysts other than MFI framework catalysts, a catalyst recycle rate can be selected to produce an average catalyst exposure time/average cycle length for catalyst in the reactor of about 25 g $CH_3OH$/g catalyst to about 200 g $CH_3OH$/g catalyst, or about 25 g $CH_3OH$/g catalyst to about 180 g $CH_3OH$/g catalyst, or about 50 g $CH_3OH$/g catalyst to about 180 g $CH_3OH$/g catalyst, or about 50 g $CH_3OH$/g catalyst to about 150 g $CH_3OH$/g catalyst, or about 25 g $CH_3OH$/g catalyst to about 100 g $CH_3OH$/g catalyst, or about 50 g $CH_3OH$/g catalyst to about 100 g $CH_3OH$/g catalyst, or about 100 g $CH_3OH$/g catalyst to about 180 g $CH_3OH$/g catalyst, or about 100 g $CH_3OH$/g catalyst to about 150 g $CH_3OH$/g catalyst. The appropriate cycle length for a catalyst including a non-MFI framework zeolite can depend on the type of zeolite.

It is noted that the oxygenate feed and/or conversion reaction environment can include water in various proportions. Conversion of oxygenates to aromatics and olefins results in production of water as a product, so the relative amounts of oxygenate (such as methanol or dimethyl ether) and water can vary within the reaction environment. Based on the temperatures present during methanol conversion, the water in the reaction environment can result in "steaming" of a catalyst. Thus, a catalyst used for conversion of oxygenates to aromatics is preferably a catalyst that substantially retains activity when steamed. Water may also be present in a feed prior to contacting the zeolite catalyst. For example, in commercial processing of methanol to form gasoline, in order to control heat release within a reactor, an initial catalyst stage may be used to convert a portion of the methanol in a feed to dimethyl ether and water prior to contacting a zeolite catalyst for forming gasoline.

Catalysts for Oxygenate Conversion

In various aspects, a transition metal-enhanced zeolite catalyst composition can be used for conversion of oxygenate feeds to naphtha boiling range fractions and olefins. In this discussion and the claims below, a zeolite is defined to refer to a crystalline material having a porous framework structure built from tetrahedra atoms connected by bridging oxygen atoms. Examples of known zeolite frameworks are given in the "Atlas of Zeolite Frameworks" published on behalf of the Structure Commission of the International Zeolite Association", 6$^{th}$ revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework.

A suitable zeolite can include a 10-member or 12-member ring pore channel network, such as a 1-dimensional 10-member ring pore channel or a 3-dimensional 10-member ring pore channel. Examples of suitable zeolites having a 3-dimensional 10-member ring pore channel network include zeolites having an MFI or MEL framework, such as ZSM-5 or ZSM-11. ZSM-5 is described in detail in U.S. Pat. No. 3,702,886 and Re. 29,948. ZSM-11 is described in detail in U.S. Pat. No. 3,709,979. Preferably, the zeolite is ZSM-5. Examples of suitable zeolites having a 1-dimensional 10-member ring pore channel network include zeolites having a MRE (ZSM-48), MTW, TON, MTT, and/or MFS framework. In some aspects, a zeolite with a 3-dimensional pore channel can be preferred for conversion of methanol, such as a zeolite with an MFI framework.

In some aspects, it may be desirable to convert methanol (and/or other oxygenates) to small olefins, such as $C_2$ and/or $C_3$ olefins. In such aspects, zeolites with 8-member rings as the largest pore channel may be suitable for the conversion reaction. SAPO-34 is an example of an 8-member ring zeolite that can convert methanol to small olefins. Other examples can include zeolites having a framework structure of CHA (such as SAPO-34), RHO, AEI, LTA, KFI, and/or DDR.

Generally, a zeolite having desired activity for methanol conversion can have a silicon to aluminum molar ratio of about 10 to about 200, or about 15 to about 100, or about 20 to about 80, or about 20 to about 40. For example, the silicon to aluminum ratio can be at least about 10, or at least about 20, or at least about 30, or at least about 40, or at least about 50, or at least about 60. Additionally or alternately, the silicon to aluminum ratio can be about 300 or less, or about 200 or less, or about 100 or less, or about 80 or less, or about 60 or less, or about 50 or less.

Typically, reducing the silicon to aluminum ratio in a zeolite will result in a zeolite with a higher acidity, and therefore higher activity for cracking of hydrocarbon or hydrocarbonaceous feeds, such as petroleum feeds. However, with respect to conversion of oxygenates to aromatics, such increased cracking activity may not be beneficial, and instead may result in increased formation of residual carbon or coke during the conversion reaction. Such residual carbon can deposit on the zeolite catalyst, leading to deactivation of the catalyst over time. Having a silicon to aluminum ratio of at least about 40, such as at least about 50 or at least about 60, can reduce or minimize the amount of additional residual carbon that is formed due to the acidic or cracking activity of a catalyst.

It is noted that the molar ratio described herein is a ratio of silicon to aluminum. If a corresponding ratio of silica to alumina were described, the corresponding ratio of silica ($SiO_2$) to alumina ($Al_2O_3$) would be twice as large, due to the presence of two aluminum atoms in each alumina stoichiometric unit. Thus, a silicon to aluminum ratio of 10 corresponds to a silica to alumina ratio of 20.

In some aspects, a zeolite in a catalyst can be present at least partly in the hydrogen form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of about 400° C. to about 700° C. to convert the ammonium form to the active hydrogen form.

Additionally or alternately, a zeolitic catalyst can include and/or be enhanced by a transition metal. Preferably the transition metal is a Group 12 metal from the IUPAC periodic table (sometimes designated as Group IIB) selected from Zn, Cd, or a combination thereof. More generally, the transition metal can be any convenient transition metal selected from Groups 6-15 of the IUPAC periodic table. The transition metal can be incorporated into the zeolite/catalyst by any convenient method, such as by impregnation, by ion exchange, by mulling prior to extrusion, and/or by any other convenient method. Optionally, the transition metal incorporated into a zeolite/catalyst can correspond to two or more metals. After impregnation or ion exchange, the transition metal-enhanced catalyst can be treated in air or an inert atmosphere at a temperature of about 400° C. to about 700° C. The amount of transition metal can be expressed as a weight percentage of metal relative to the total weight of the catalyst (including any zeolite and any binder). A catalyst can include about 0.05 wt % to about 20 wt % of one or more transition metals, or about 0.1 wt % to about 10 wt %, or about 0.1 wt % to about 5 wt %, or about 0.1 wt % to about 2.0 wt %. For example, the amount of transition metal can be at least about 0.1 wt % of transition metal, or at least about 0.25 wt % of transition metal, or at least about 0.5 wt %, or at least about 0.75 wt %, or at least about 1.0 wt %. Additionally or alternately, the amount of transition metal can be about 20 wt % or less, or about 10 wt % or less, or about 5 wt % or less, or about 2.0 wt % or less, or about 1.5 wt % or less, or about 1.2 wt % or less, or about 1.1 wt % or less, or about 1.0 wt % or less.

In some optional aspects, a zeolitic catalyst can be substantially free of phosphorous. A catalyst composition that is substantially free of phosphorous can contain about 0.01 wt % of phosphorous or less, such as less than about 0.005 wt % of phosphorous, or less than about 0.001 wt % of phosphorous. A zeolitic catalyst that is substantially free of phosphorous can be substantially free of intentionally added phosphorous or substantially free of both intentionally added phosphorous as well as phosphorous present as an impurity in a reagent for forming the catalyst composition. In some aspects, a zeolitic catalyst can contain no added phosphorous, such as containing no intentionally added phosphorous and/or containing no phosphorous impurities to within the detection limits of standard methods for characterizing a reagent and/or a resulting zeolite.

Optionally, a zeolitic catalyst for methanol conversion can include added phosphorus, such as phosphorus added by impregnation, ion exchange, mulling prior to extrusion, or another convenient method. The amount of phosphorus can be related to the amount of transition metal in the catalyst composition. In some aspects, the molar ratio of phosphorus to transition metal can be 0.5 to 5.0, or 1.5 to 3.0, or 1.0 to 2.5, or 1.5 to 2.5. At higher molar ratios of phosphorus to transition metal, the phosphorus can be beneficial for maintaining a relatively stable selectivity for aromatics formation during an oxygenate conversion process. Additionally or alternately, a catalyst can include about 0.05 wt % to about 10 wt % of phosphorus, or about 0.1 wt % to about 10 wt %, or about 0.1 wt % to about 5 wt %, or about 0.1 wt % to about 2.0 wt %. For example, the amount of phosphorus can be at least about 0.1 wt %, or at least about 0.25 wt %, or at least about 0.5 wt %, or at least about 0.75 wt %, or at least about 1.0 wt %. Additionally or alternately, the amount of phosphorus can be about 10 wt % or less, or about 5 wt % or less, or about 2.0 wt % or less, or about 1.5 wt % or less, or about 1.2 wt % or less, or about 1.1 wt % or less, or about 1.0 wt % or less.

A catalyst composition can employ a transition metal-enhanced zeolite in its original crystalline form or after formulation into catalyst particles, such as by extrusion. A process for producing zeolite extrudates in the absence of a binder is disclosed in, for example, U.S. Pat. No. 4,582,815, the entire contents of which are incorporated herein by reference. Preferably, the transition metal can be incorporated after formulation of the zeolite (such as by extrusion) to form self-bound catalyst particles. Optionally, a self-bound catalyst can be steamed after extrusion. The terms "unbound" and "self-bound" are intended to be synonymous and mean that the present catalyst composition is free of any of the inorganic oxide binders, such as alumina or silica, frequently combined with zeolite catalysts to enhance their physical properties.

The transition metal-enhanced zeolite catalyst composition employed herein can further be characterized based on activity for hexane cracking, or Alpha value. Alpha value is a measure of the acid activity of a zeolite catalyst as compared with a standard silica-alumina catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of about 538° C. and a variable flow rate as described in detail in the Journal of Catalysis, Vol. 61, p. 395. Higher alpha values correspond with a more active cracking catalyst. For an oxygenate conversion catalyst, Alpha values of at least 15 can be suitable, with alpha values greater than 100 being preferred. In particular, the Alpha value can be about 15 to about 1000, or about 50 to about 1000, or about 100 to about 1000.

As an alternative to forming self-bound catalysts, zeolite crystals can be combined with a binder to form bound catalysts. Suitable binders for zeolite-based catalysts can include various inorganic oxides, such as silica, alumina, zirconia, titania, silica-alumina, cerium oxide, magnesium oxide, yttrium oxide, or combinations thereof. For catalysts including a binder, the catalyst can comprise at least about 10 wt % zeolite, or at least about 30 wt %, or at least about 50 wt %, such as up to about 90 wt % or more. Generally, a binder can be present in an amount between about 1 wt % and about 90 wt %, for example between about 5 wt % and about 40 wt % of a catalyst composition. In some aspects, the catalyst can include at least about 5 wt % binder, such as at least about 10 wt %, or at least about 20 wt %. Additionally or alternately, the catalyst can include about 90 wt % or less of binder, such as about 50 wt % or less, or about 40 wt % or less, or about 35 wt % or less. Combining the zeolite and the binder can generally be achieved, for example, by mulling an aqueous mixture of the zeolite and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

In some aspects, a binder can be used that is substantially free of alumina, such as a binder that is essentially free of alumina. In this description, a binder that is substantially free of alumina is defined as a binder than contains about 10 wt % alumina or less, such as about 7 wt % or less, or about 5 wt % or less, or about 3 wt % or less. A binder that is essentially free of alumina is defined as a binder that contains about 1 wt % or less, such as about 0.5 wt % or less, or about 0.1 wt % or less. In still other aspects, a binder can be used that contains no intentionally added alumina and/or that contains no alumina within conventional detection limits for determining the composition of the binder and/or the reagents for forming the binder. Although alumina is commonly used as a binder for zeolite catalysts, due in part to ease of formulation of alumina-bound catalysts, in some aspects the presence of alumina in the binder can reduce or inhibit the activity of a transition metal-enhanced zeolite for converting methanol to aromatics. For example, for a catalyst where the transition metal is incorporated into the catalyst after formulation of the bound catalyst (such as by extrusion), the transition metal may have an affinity for exposed alumina surfaces relative to exposed zeolite surfaces, leading to increased initial deposition and/or migration of transition metal to regions of the bound catalyst with an alumina surface in favor of regions with a zeolite surface. Additionally or alternately, alumina-bound catalysts can tend to have low micropore surface area, meaning that the amount of available zeolite surface available for receiving a transition metal may be undesirably low.

As an example of forming a bound catalyst, the following procedure describes a representative method for forming silica bound ZSM-5 catalyst particles. ZSM-5 crystal and a silica binder, such as an Ultrasil silica binder, can be added to a mixer and mulled. Additional deionized water can be added during mulling to achieve a desired solids content for extrusion. Optionally, a caustic solution can also be added to the mixture and mulled. The mixture can then be extruded into a desired shape, such as $\frac{1}{10}$" quadralobes. The extrudates can be dried overnight at about 250° F. (121° C.) and then calcined in nitrogen for about 3 hours at about 1000° F. (538° C.). The extrudates can then be exchanged twice with an about 1N solution of ammonium nitrate. The exchanged crystal can be dried overnight at about 250° F. (121° C.) and then calcined in air for about 3 hours at about 1000° F. (538° C.). This results in a silica bound catalyst. Based on the exchange with ammonium nitrate and subsequent calcinations in air, the ZSM-5 crystals in such a bound catalyst can correspond to ZSM-5 with primarily hydrogen atoms at the ion exchange sites in the zeolite. Thus, such a bound catalyst is sometimes described as being a bound catalyst that includes H-ZSM-5.

To form a transition metal-enhanced catalyst, a bound catalyst can be impregnated via incipient wetness with a solution containing the desired metal for impregnation, such as Zn or P. The impregnated crystal can then be dried overnight at about 250° F. (121° C.), followed by calcination in air for about 3 hours at about 1000° F. (538° C.). More generally, a transition metal can be incorporated into the zeolitic catalyst at any convenient time, such as before or after ion exchange to form H-form crystals, or before or after formation of a bound extrudate. In some aspects that are preferred from a standpoint of facilitating manufacture of a bound zeolite catalyst, the transition metal can be incorporated into the bound catalyst (such as by impregnation or ion exchange) after formation of the bound catalyst by extrusion or another convenient method.

Example of Reaction System Configuration

FIG. 1 shows an example of a reaction system configuration for performing oxygenate conversion to form a naphtha boiling range product. The reactors shown in FIG. 1 can correspond to moving bed reactors and/or fluidized bed reactors and/or another type of reactor configuration where catalyst can be introduced into catalyst inventory and removed from catalyst inventor while feed is being processed in the reactor. The reactors in FIG. 1 are shown as downflow reactors for convenience, and in other aspects the reactors can have any convenient configuration, such as an upflow configuration. In FIG. 1, a feed 105 can correspond to an oxygenate-containing feed. Optionally, oxygenate feed 105 can be introduced into a reactor as a plurality of input flows, such as a first input flow containing a mixture of methanol and water and a second input flow containing a mixture of nitrogen and hydrogen.

The feed 105 can optionally be introduced into an initial dehydration reactor 110. Initial dehydration reactor 110 can include an acidic catalyst, such as an acidic alumina catalyst, that can facilitate an equilibrium reaction between methanol, water, and dimethyl ether. This can result in production of an effluent 115 that includes both methanol and dimethyl ether. Those of skill in the art will recognize that dimethyl ether and methanol can often be used in similar manners when performing an oxygenate conversion reaction. The dehydration of methanol to form dimethyl ether is highly exothermic. By performing an initial dehydration, the amount of heat generated in the to conversion reactor(s) can be reduced, which can allow for improved temperature control in the conversion reactor. Optionally, a portion of the oxygenate feed 105 can bypass the dehydration reactor and can be input directly into conversion reactor 120. In aspects where other oxygenates are used as a feed, such as $C_{2+}$ alcohols or larger ethers, dehydration reactor can be omitted so that feed 105 (or a combination of oxygenate feed 105 and olefinic feed 106) is an input flow for conversion reactor 120.

The oxygenate feed 105 (and/or the effluent 115 containing both dimethyl ether and methanol) can then be passed into conversion reactor 120. The input to conversion reactor 120 can be exposed to a conversion catalyst under effective conditions for forming a conversion effluent 125. The conversion effluent 125 can then be separated, such as by using a 3 phase separator 130. One phase generated by separator 130 can be an aqueous phase 133 that includes a substantial majority of the water present within the conversion effluent 125. Another phase generated by separator 130 can correspond to a hydrocarbon liquid product 137. The hydrocarbon liquid product can correspond to naphtha boiling range compounds formed during the conversion reaction. Optionally, the hydrocarbon liquid product can include a portion of hydrocarbon-like compounds that include one or more heteroatoms, such as oxygen, sulfur, nitrogen, and/or other heteroatoms that are commonly found in petroleum or bio-derived feeds.

A third phase generated by separator 130 can correspond to a hydrocarbon gas product 135. The hydrocarbon gas product 135 can include $C_{4-}$ compounds corresponding to light paraffins and light olefins. Optionally, a recycle portion 122 of hydrocarbon gas product 135 can be recycled as part of the input flows to conversion reactor 120. In some configurations where the amount of recycle portion 122 is sufficiently large, a bleed or waste flow (not shown) can also be present to reduce or minimize the build-up of $C_{4-}$ paraffins in conversion reactor 120.

Figure 9:
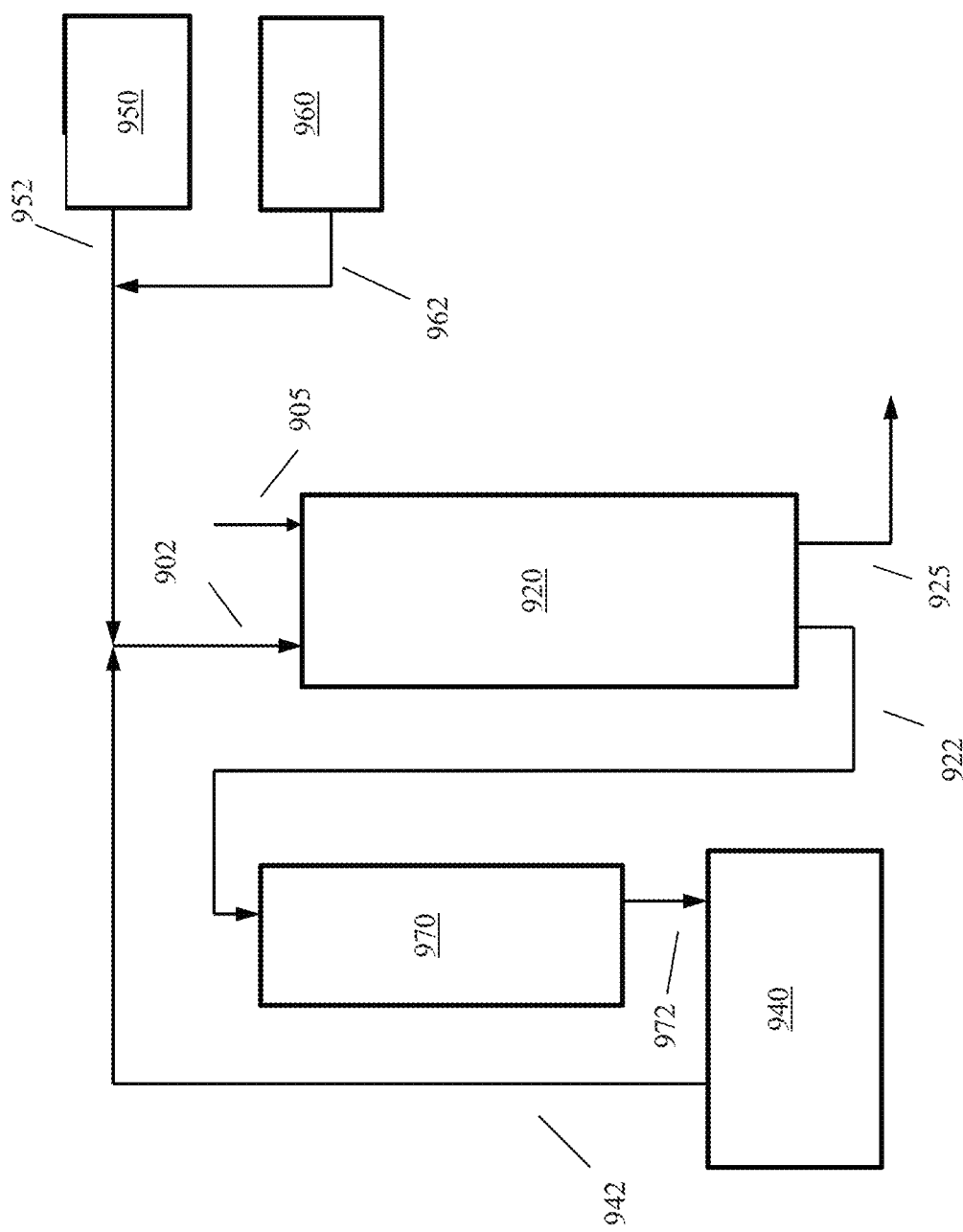
FIG. 9 schematically shows an example of a reaction system including a conversion reactor.

FIG. 9 shows another example of a reaction system for processing a methanol-containing feed and/or another type of oxygenate-containing feed. The reaction system in FIG. 9 corresponds to the catalyst stores, reactor, and regenerator for a reaction system for conversion of oxygenates to aromatics and/or olefins. In FIG. 9, a feed 905 and a catalyst flow 902 are introduced into reactor 920. The reactor configuration shown in FIG. 9 corresponds to a co-current flow moving bed reactor. In other aspects, a fluidized bed reactor and/or another type of reactor that can allow for catalyst addition and withdrawal during processing can be used. The feed 905 is exposed to catalyst within reactor under conversion conditions suitable for forming a converted effluent 925. Optionally, the feed 905 can correspond to a feed that has been partially dehydrated to form dimethyl ether (not shown).

Catalyst flow 902 can correspond to a combination of make-up catalyst and catalyst that has been regenerated in regenerator 970. In the example shown in FIG. 9, catalyst store 950 and catalyst store 960 can represent storage containers (such as lock hoppers) for fresh catalyst corresponding to two separate catalyst systems. After determining a desired change in the reactivity for reactor 920, an amount of make-up catalyst from catalyst store 950 and/or catalyst store 960 can be introduced into reactor 920 as part of catalyst flow 902. The (fresh) catalyst particles in catalyst store 950 and catalyst store 960 can correspond to any convenient type of catalyst system, such as a single catalyst or a mixture of catalysts. In some aspects, catalyst stores 950 and 960 can instead introduce catalyst into inventory catalyst store 940, so that catalyst flow 902 corresponds to a catalyst flow 942 derived from inventory catalyst store 940. In the example shown in FIG. 9, catalyst flow 902 can correspond to a mixture of catalyst flow 942 from inventory catalyst store 940 and at least one of catalyst flow 952 and catalyst flow 962 (from catalyst store 950 and catalyst store 960, respectively). In some aspects, the combined amount of catalyst flow 952 and catalyst flow 962 can correspond to a rate of make-up catalyst addition per day of at least 5 wt % of the catalyst inventory in the reaction system, or at least 10 wt %, or at least 20 wt %, such as up to 50 wt % or more.

After exposure to feed 905 to form converted effluent 925, catalyst can exit reactor 920 as part of catalyst flow 922. Catalyst flow 922 can then be passed into regenerator 970 for full or partial regeneration of the catalyst. Optionally, a portion of catalyst flow 922 can be withdrawn from the reaction system (not shown) either before or after regenerator 970. After regeneration, the regenerated catalyst flow 972 can be passed into inventory catalyst store 940. In some aspects, inventory catalyst store 940 may simply correspond to a pipe of sufficient volume to allow the total catalyst inventory in the reaction system to be contained within the combination of reactor 920, regenerator 970, and the corresponding pipes connecting the reactor 920 and the regenerator 970.

Example 1—Methanol Conversion Using P/Zn-ZSM-5

The conversion catalyst used in this example was based on small crystal, self-bound MFI framework (ZSM-5) zeolite. The ZSM-5 had a silicon to aluminum ratio of 20 to 40 and an Alpha value of at least 100. After making an H-form extrudate of the self-bound zeolite, Zn and P were added via aqueous impregnation of $Zn(NO_3)_2$ and $H_3PO_4$. Sufficient amounts of Zn and P were added to produce a catalyst with about 1.0 wt % loading of each of Zn and P. This catalyst can be referred to as a P/Zn-ZSM-5 catalyst. The Zn and P were added by serial impregnation (Zn first), but in other aspects co-impregnation may be used. More generally, in various aspects other promoters from Groups 6-15 of the IUPAC periodic table may be used in place of and/or in addition to Zn and P.

The conversion catalyst was tested in an adiabatic fixed-bed reactor with recycle of the produced light gas back into the reactor. The reactor configuration was similar to FIG. 1, but all of the hydrocarbon gas product 135 was used for recycle stream 122. The feed into the dehydration reactor corresponded to 96 wt % methanol and 4 wt % water. The flow rate was sufficient to produce a liquid hourly space velocity of 1.66 $h^{-1}$ based on the weight of catalyst in the (second) conversion reactor. The dehydration reactor included an acidic alumina catalyst to dehydrate the methanol into an equilibrium mixture of methanol, water, and dimethyl ether. The equilibrium mixture was then passed into the conversion reactor, which contained the P/Zn-ZSM-5 catalyst described above. The effluent from the conversion reactor corresponded to a mixture including water, olefins, paraffins, aromatics, and hydrogen. The heavy portion of the reactor product, mainly $C_{5+}$ and water, was removed in a vapor-liquid separator. The remaining light gasses were recycled to the inlet of the conversion reactor. The reaction conditions were chosen to manage the adiabatic temperature rise of the reactor and the composition of the final product.

Table 1 shows the reaction conditions that were tested. The columns starting with "MTA1" corresponded to tests performed starting with fresh catalyst. The catalyst was then regenerated and exposed to the feed under the "MTA2" conditions. In between the MTA1 and MTA2 conditions, an oxidative catalyst regeneration was performed to remove coke from the catalyst. Inlet T and Outlet T refer to the temperatures at the inlet and outlet of the conversion reactor. The pressure and WHSV also refer to conditions in the conversion reactor. In two of the tests, an additional diluent flow of $N_2$ was added. For MTA2-2, about 5 mol % of the fresh feed to the reactor corresponded to $N_2$, with the rest of the feed corresponding to the methanol/water mixture. However, because of buildup of $N_2$ due to (essentially) full recycle of the hydrocarbon gas stream, the net $N_2$ content in the feed into the reactor was about 24 mol % (corresponds to roughly 22 wt %). For MTA2-3, about 8.5 mol % of the fresh feed corresponded to $N_2$, which resulted in a net or total content of $N_2$ in the feed of about 40 mol % (corresponds to roughly 36 wt %).

TABLE 1

Test conditions for conversion in presence of P/Zn-ZSM-5

|  | MTA1-1 | MTA1-2 | MTA1-3 | MTA2-1 | MTA2-2 | MTA2-3 | MTA2-4 |
| --- | --- | --- | --- | --- | --- | --- | --- |
| Inlet T (° C.) | 400 | 400 | 450 | 400 | 400 | 450 | 450 |
| Outlet T (° C.) | 500 | 500 | 525 | 500 | 500 | 525 | 525 |
| Pressure (kPag) | ~1000 | ~1000 | ~1000 | ~1000 | ~500 | ~500 | ~500 |
| WHSV ($hr^{-1}$) | 2.0 | 1.0 | 1.0 | 2.0 | 2.0 | 1.0 | 1.0 |
| $N_2$ flow | 0 | 0 | 0 | 0 | yes | yes | 0 |

Figure 2:
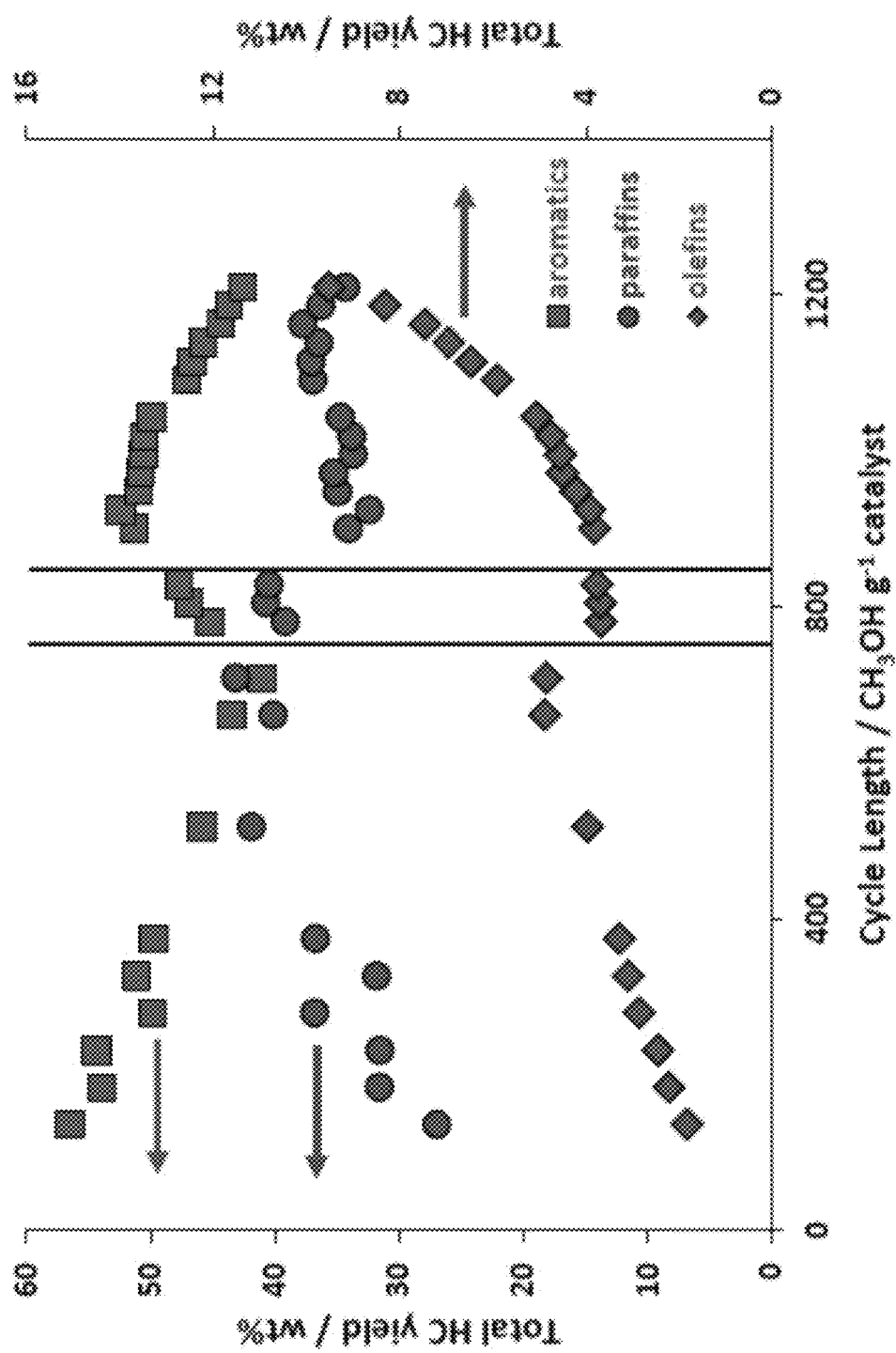
FIG. 2 shows relative yields in the total hydrocarbon product from conversion of methanol in the presence of a P/Zn-ZSM-5 catalyst.
Figure 3:
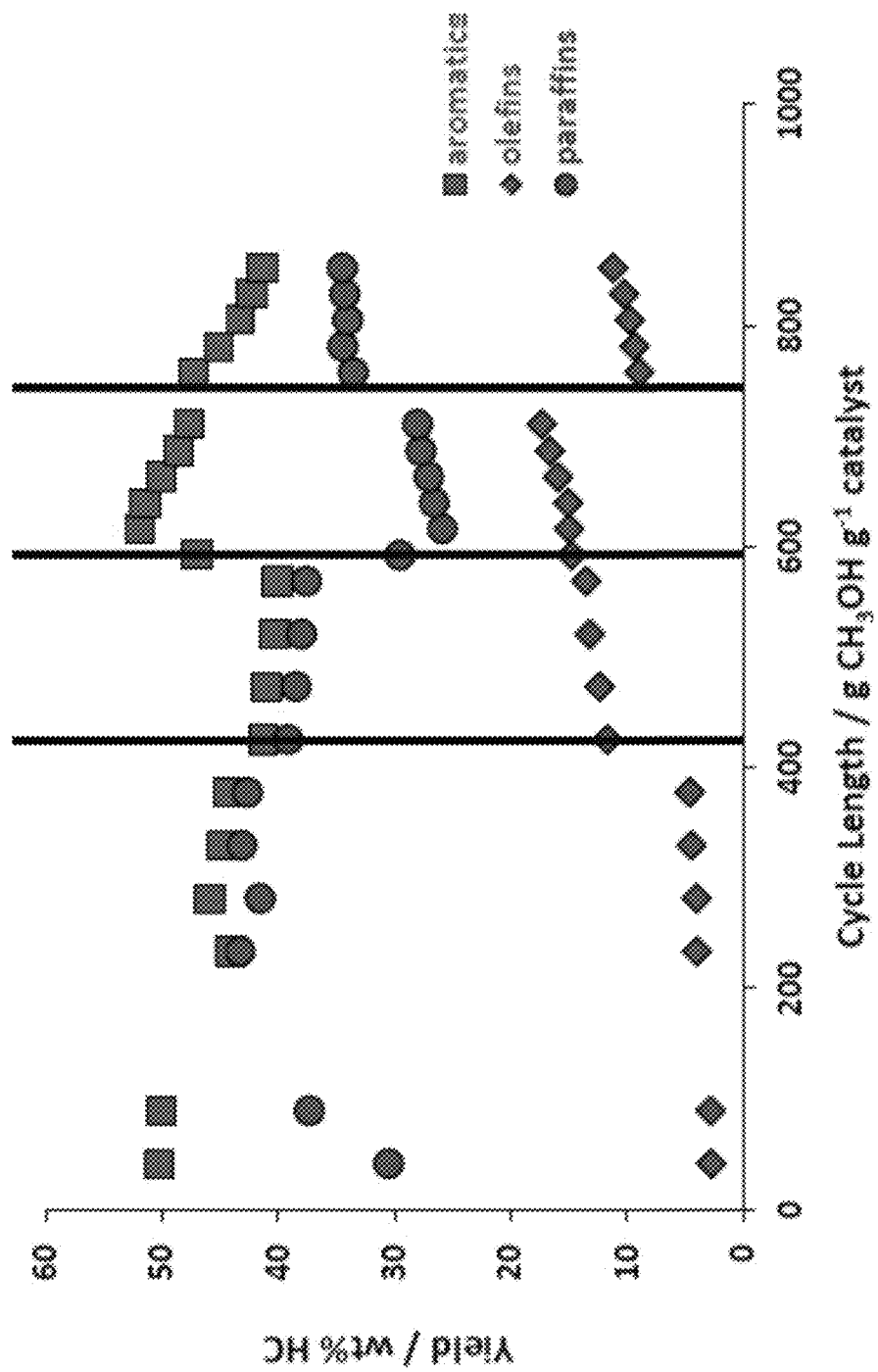
FIG. 3 shows relative yields in the total hydrocarbon product from conversion of methanol in the presence of a P/Zn-ZSM-5 catalyst.

FIG. 2 shows the product distribution for the total hydrocarbon product from the MTA1 tests, corresponding to conditions MTA1-1, MTA1-2, and MTA1-3 in Table 1. In FIG. 3, the squares correspond to aromatic yield, the circles correspond to paraffin yield, and the diamonds correspond to olefin yield. As shown in FIG. 2, the yield of aromatics was generally between 40 wt % and 60 wt % of the total hydrocarbon product. The amount of paraffins ranged from roughly 30 wt % to roughly 45 wt %. It is noted that about 60 wt % of the paraffins corresponded to $C_3$ and $C_4$ paraffins, while another 20 wt % of the paraffins corresponded to $C_{5+}$ paraffins that could be included as part of a naphtha boiling range product. Toward the end of the MTA1-3 test condition, where the cycle length was greater than 1000 grams of methanol per gram of catalyst, the amount of olefins produced started to increase sharply from the roughly 5 wt % to 15 wt % observed early in the tests to upward of 20 wt % or even 30 wt %. This late increase in olefin selectivity appeared to come at the expense of aromatic selectivity.

FIG. 3 provides a product distribution for the MTA2 tests similar to the product distribution shown in FIG. 2. MTA2-1 represents a test condition similar to MTA1-1, to allow for comparison of catalyst activity between fresh catalyst and regenerated catalyst. The olefin selectivity for MTA2-1 was slightly lower than the olefin selectivity for MTA1-1, but otherwise the product selectivities were similar for use of fresh and regenerated catalyst under similar conditions. This demonstrates that the catalyst can be effectively regenerated to a condition similar to original activity. It is noted that the addition of diluent at the lower reactor pressure (~500 kPag) in test condition MTA2-3 resulted in a reduction in paraffin selectivity in favor of production of aromatics and olefins.

Further analysis was performed on the total hydrocarbon product from test MTA2-3 to determine the relative distribution of olefins and paraffins in the lighter portions of the effluent. As shown in FIG. 3, test condition MTA2-3 resulted in production of roughly 20 wt % olefins and roughly 30 wt % paraffins. The first column in Table 2 shows the selectivity for each carbon number of olefin ($C_2$ to $C_6$) within the olefins produced at test condition MTA-3. For example, within the 20 wt % of olefins produced at test condition MTA2-3, about 39 wt % corresponded to $C_3$ olefins and about 26 wt % corresponded to $C_4$ olefins. Similarly, the second column in Table 2 shows the selectivity for each carbon number of paraffin ($C_1$ to $C_6$) within the paraffins produced at test condition MTA2-3.

TABLE 2

Olefin vs Paraffin Selectivity

|  | Olefin | Paraffin |
| --- | --- | --- |
| C1 |  | 9 |
| C2 | 19 | 9 |
| C3 | 39 | 37 |
| C4 | 26 | 27 |
| C5 | 13 | 14 |
| C6 | 3 | 5 |

Additional characterization of products was performed for the effluents from test runs MTA1-1, MTA1-3, and MTA2-3. Table 3 shows the naphtha boiling range product yield, octane rating for the naphtha boiling range product, and distillate fuel boiling range product yield for the effluents from runs MTA1-1, MTA1-3, and MTA2-3. As shown in Table 3, all of the naphtha products had octane ratings of at least 95 and provided naphtha yields of at least 55 wt % relative to the weight of the total hydrocarbon product in the conversion effluent. It is noted that Table 3 also includes a "distillate yield" for each condition. The distillate yields in Table 3 do not represent distillate that was made during the test condition, as the amount of distillate produced during the conversion reaction was essentially 0. Instead, the "distillate yield" values in Table 3 represent the amount of olefins generated that exited from the reactor with the liquid product. These olefins would be suitable for oligomerization in a subsequent oligomerization step, and therefore represented a potential distillate yield at each condition.

TABLE 3

Conversion Effluent Fuel Yields

|  | Naphtha yield (wt %) | Octane: (RON + MON)/2 | "Distillate yield" (wt %) |
| --- | --- | --- | --- |
| MTA1-1 | ~60 | >100 | ~1 |
| MTA1-3 | ~55 | >95 | ~8 |
| MTA2-3 | ~55 | >97 | ~15 |

Example 2—Influence of Type of Conversion Catalyst on Conversion Reaction

In this example, self-bound ZSM-5 similar to the catalyst in Example 1, but without Zn or P as promoters, was tested along with several other conversion catalysts. The additional catalysts corresponded to self-bound ZSM-48 with a roughly 45 to 1 silicon to aluminum ratio; self-bound ZSM-48 dopes with $Y_2O_3$; alumina bound ITQ-13; and self-bound ZSM-5 with 0.5 wt % Zn as a promoter. The catalysts were investigated in an apparatus similar to the apparatus used in Example 1, but without the light gas recycle. Instead, the apparatus for Example 2 was configured as an isothermal reactor. The feed was similar to the feed in Example 1, and the reactor conditions included a reactor temperature of 450° C., a reactor pressure of ~100 kPag, and a WHSV of about 2.0 $hr^{-1}$.

Figure 4:
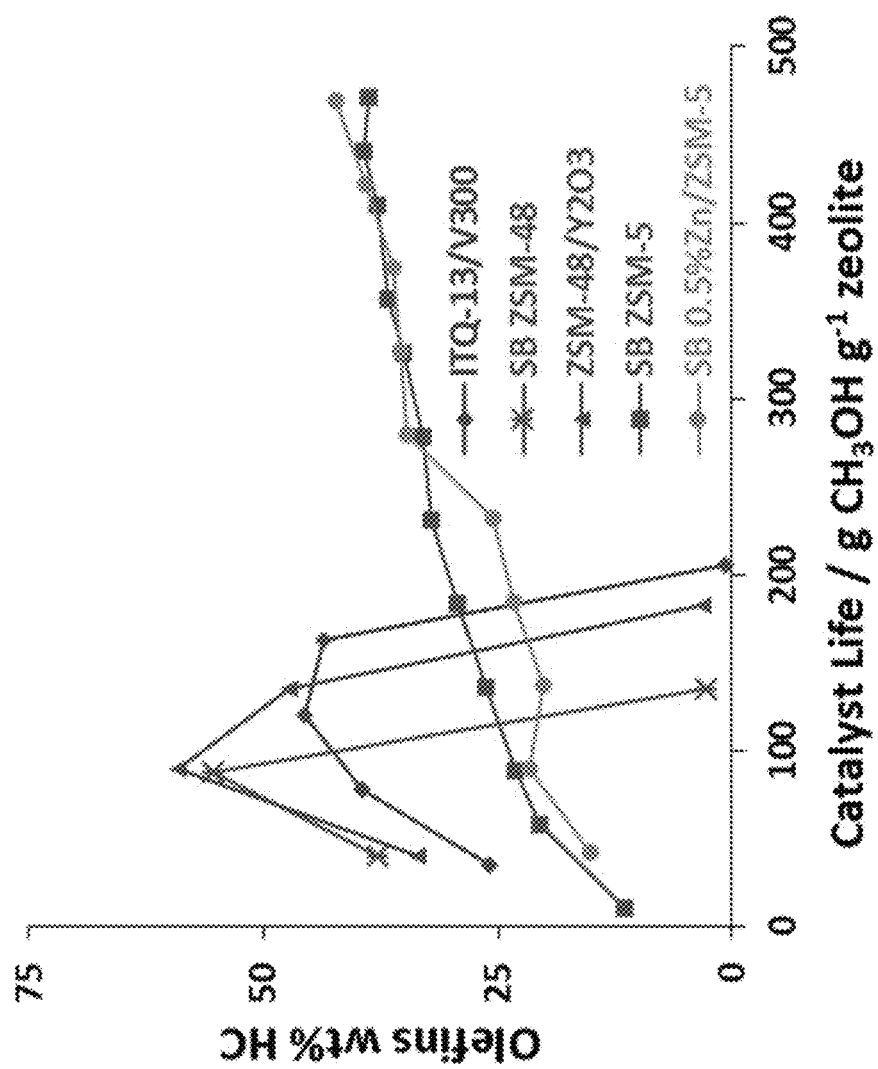
FIG. 4 shows olefin selectivity as a function of cycle length for conversion of methanol in the presence of various catalysts.

FIG. 4 shows the olefin selectivity as a function of cycle length for the tests with each catalyst. As shown in FIG. 4, the self-bound ZSM-5 catalysts (both without promoter and with 0.5 wt % Zn) provided stable activity over the full cycle length that was investigated. By contrast, the other types of catalysts provided increased selectivity at low cycle lengths, ranging from fresh (or freshly regenerated) catalyst to about 100 or 200 grams of methanol per gram of catalyst. At longer cycle lengths, however, the olefin selectivity dropped dramatically.

Figure 5:
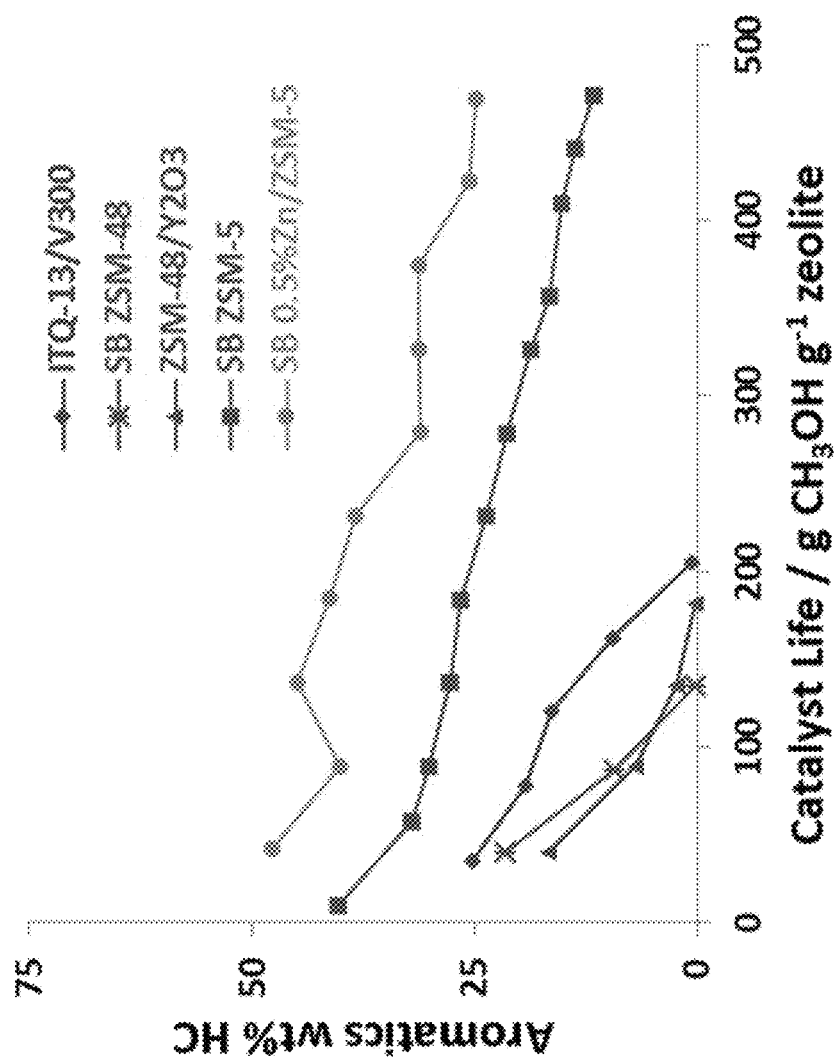
FIG. 5 shows aromatic selectivity as a function of cycle length for conversion of methanol in the presence of various catalysts.

FIG. 5 shows the aromatic selectivity as a function of cycle length for the tests with each catalyst. For the catalysts other than ZSM-5, the selectivity for aromatic formation starts at about 25 wt % or less at a cycle length of about 50 grams of methanol per gram of catalyst, and then drops until little or no aromatic formation occurs. By contrast, the ZSM-5 catalysts provide a higher aromatic selectivity initially, and the rate of reduction of aromatic selectivity is more gradual. The selectivity for aromatic formation was higher for the 0.5 wt % Zn promoted ZSM-5, and the relative selectivity increase of about 5 wt % to 10 wt % was maintained over the range of cycle lengths included in FIG. 5.

Figure 6:
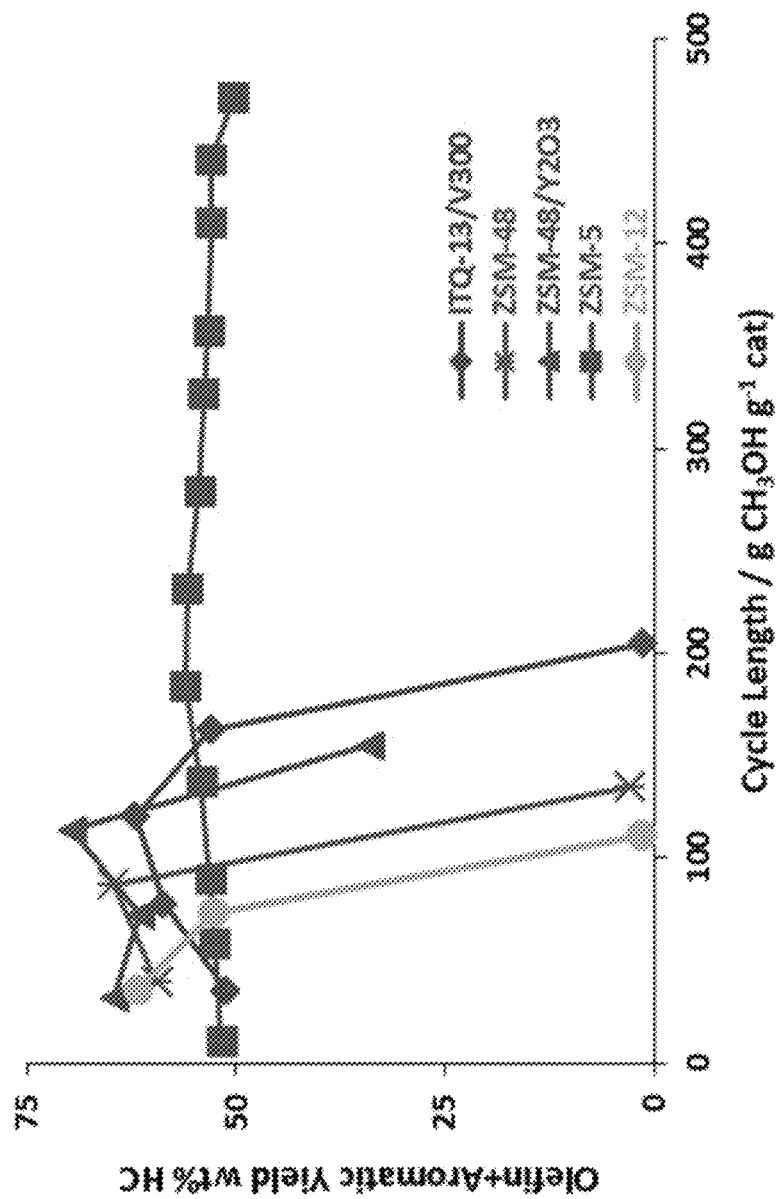
FIG. 6 shows combined aromatic and olefin selectivity as a function of cycle length for conversion of methanol in the presence of various catalysts.

FIG. 6 shows combined aromatic and olefin selectivity for the non-promoted catalysts shown in FIG. 4 and FIG. 5. The combined aromatic and olefin selectivity is also shown for an additional self-bound zeolite catalyst (ZSM-12). FIG. 6 shows that the combined olefin and aromatic yield for the ZSM-5 catalyst remains relatively constant over the range of cycle lengths shown in FIG. 6.

The data in FIG. 4, FIG. 5, and FIG. 6 demonstrate that a reactor that can allow for in-situ regeneration of catalyst can provide an additional method for control of a conversion reaction using either a ZSM-5 catalyst or another type of zeolite. For zeolites other than MFI framework structure zeolites, a moving bed or fluidized bed reactor with catalyst regeneration can be used to control the average cycle length for the catalyst in the reactor to a value between about 50 grams to about 150 grams of methanol per gram of catalyst. For MFI framework structure zeolites, a broader range of average cycle lengths can be suitable. If greater aromatic production is desired, a shorter average cycle length can be selected, such as an average cycle length of about 50 grams to about 250 grams of methanol per gram of catalyst, or about 50 grams to about 200 grams, or about 100 grams to about 250 grams. If greater olefin product is desired, a longer average cycle length can be selected, such as an average cycle length of about 250 grams to about 500 grams of methanol per gram of catalyst, or about 300 grams to about 500 grams.

Example 3—Influence of Metal Loadings on Conversion

ZSM-5 self-bound catalyst similar to the catalyst in Example 1 was impregnated with Zn to achieve metal loadings of 0.5 wt % Zn, 1.0 wt % Zn, and 3.0 wt % Zn relative to the total weight of the catalyst. The catalysts with the various Zn loadings and the self-bound catalyst without Zn were then used for methanol conversion in an apparatus similar to the apparatus in Example 2. The feed was similar to the feed in Example 1, and the reactor conditions included a reactor temperature of 450° C., a reactor pressure of ~100 kPag, and a WHSV of about 2.0 $h^{-1}$.

Figure 7:
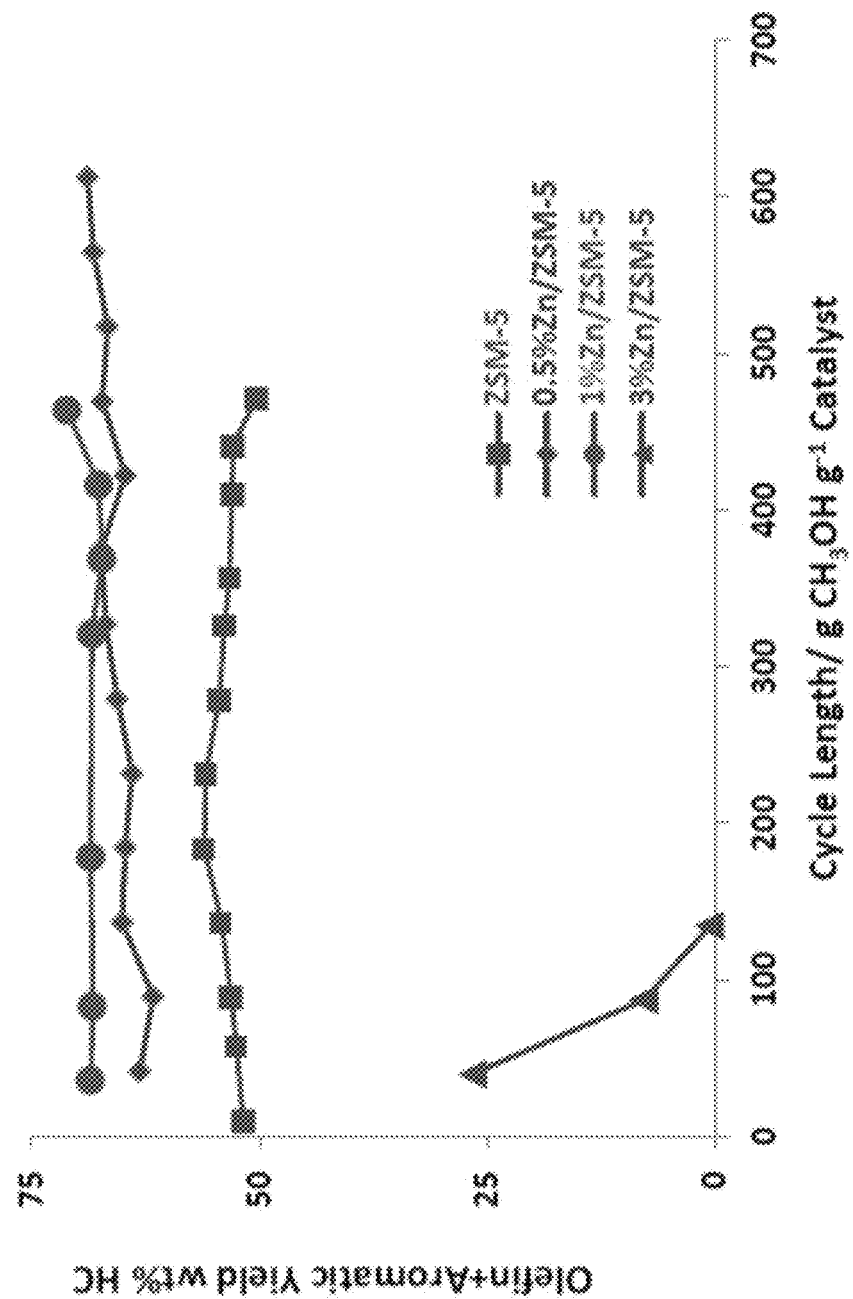
FIG. 7 shows combined aromatic and olefin selectivity as a function of cycle length for conversion of methanol in the presence of ZSM-5 catalysts with various metal loadings.

FIG. 7 shows combined olefin and aromatic yields relative to cycle length from the testing of the ZSM-5 catalysts with various Zn loadings. As shown in FIG. 7, addition of 0.5 wt % or 1.0 wt % Zn on the catalyst resulted in an increase in combined olefins and aromatics yield from 50 wt % to 55 wt % for the non-promoted ZSM-5 to 65 wt % to 75 wt % for the Zn-promoted ZSM-5 catalysts. These combined yields were also relatively stable as the average cycle length for the catalyst was increased. However, increasing the Zn loading further to 3.0 wt % Zn resulted in a sharp drop in activity, so that little or no combined olefins and aromatics were produced at cycle lengths of about 150 grams or more of methanol per gram of catalyst.

Example 4—Influence of Phosphorus Loadings on Conversion

ZSM-5 self-bound catalyst similar to the catalyst in Example 1 was impregnated with Zn to achieve a Zn loading of 1.0 wt %. Various catalyst samples were then impregnated with phosphorus to achieve relative molar phosphorus loadings of 0.8 mol P/mol Zn, 2.4 moles P/mol Zn, and 4.5 mol P/mol Zn. After forming the various catalysts with either a 1.0 wt Zn loading or both a Zn and P loading, a sample of each type of catalyst was steamed for 24 hours at 1000° F. (538° C.) in a 100% steam environment. The steaming was believed to be representative of aging that a catalyst would experience during processing. Both steamed and unsteamed versions of the catalyst with 1.0 wt % Zn and the various catalysts with both Zn and P loadings were then used for methanol conversion in an apparatus similar to the apparatus in Example 2. The feed was similar to the feed in Example 1, and the reactor conditions included a reactor temperature of 500° C., a reactor pressure of ~100 kPag, and a WHSV of about 20 $hr^{-1}$. The conditions allowed for 100% conversion of the methanol in the feed.

Figure 8:
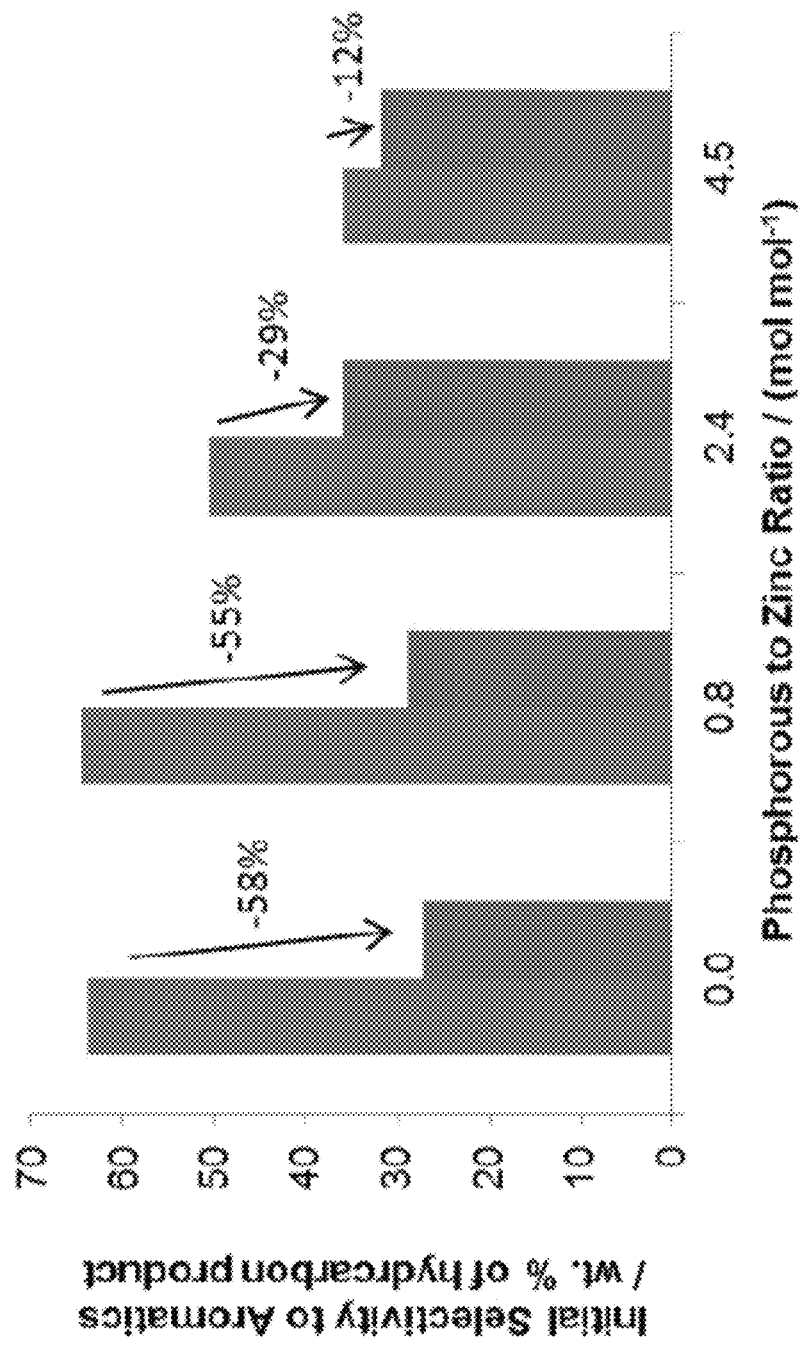
FIG. 8 shows aromatic selectivity for conversion of methanol in the presence of ZSM-5 catalysts with various phosphorus loadings.

FIG. 8 shows a comparison of the aromatic selectivity for the unsteamed and steamed versions of each catalyst. The left bar in each pair of bars represents the initial selectivity for aromatic formation of the unsteamed version of each catalyst. The right bar in each pair of bars represents the corresponding activity of the steamed version of the catalyst. As shown in FIG. 8, a phosphorus loading of at least about 2.0 mol P/mol Zn, or at least about 2.4, can allow a catalyst to retain a higher percentage of initial selectivity for aromatics. Although the initial selectivity for aromatics is somewhat reduced for unsteamed catalysts with at least 2.0 mol P/mol Zn, the aromatic selectivity for the steamed catalyst is still greater than the aromatic selectivity for a steamed catalyst having less than 2.0 mol P/mol Zn. This steaming data is believed to correlate with expected aromatic selectivity for catalysts at long cycle lengths.

Additional Embodiments

Embodiment 1

A method for forming a hydrocarbon composition, comprising: introducing catalyst particles comprising a first catalyst system at a first catalyst addition rate per day into a reaction system comprising a reactor, the reaction system comprising an inventory volume of catalyst particles of a second catalyst system, a composition of the second catalyst system being distinct from a composition of the first catalyst system by at least 5 wt %, the first catalyst addition rate per day comprising at least about 5 vol % of the inventory volume; exposing a feed comprising oxygenates to conversion catalyst in the reactor at conversion conditions to form a converted effluent comprising a hydrocarbon fraction, the conversion catalyst comprising at least a portion of the first catalyst system and at least a portion of the second catalyst system, the conversion catalyst optionally comprising at least a first catalyst and a second catalyst, the exposing the feed comprising oxygenates to a conversion catalyst optionally comprising exposing the feed comprising oxygenates to the conversion catalyst in a fluidized bed reactor, a moving bed reactor, a riser reactor, or a combination thereof.

Embodiment 2

The method of Embodiment 1, wherein the conversion catalyst in the reactor comprises the first catalyst having a first average catalyst exposure time and the second catalyst having a second average catalyst exposure time, a selectivity of the first catalyst for aromatics at the conversion conditions being at least 10 wt % greater than a selectivity of the second catalyst for aromatics at the conversion conditions.

Embodiment 3

The method of any of the above embodiments, wherein the second catalyst system comprises the first catalyst and the second catalyst, the method further comprising regenerating at least a portion of the conversion catalyst exposed to the feed comprising oxygenates, the regenerated second catalyst comprising at least 0.1 wt % of coke, or 0.1 wt % to 10 wt % of coke, or 1.0 wt % to 25 wt % of coke, the regenerated first catalyst optionally comprising 0.1 wt % or less of coke.

Embodiment 4

The method of any of the above embodiments, wherein at least one of the first catalyst system and the second catalyst system comprises at least 10 wt % of catalyst particles comprising a zeolite having MFI framework structure, the zeolite having a silicon to aluminum ratio of 10 to 200 and an Alpha value of at least 5.

Embodiment 5

The method of Embodiment 4, wherein the at least 10 wt % of catalyst particles further comprises 0.1 wt % to 3.0 wt % of a transition metal supported on the catalyst particles, the 0.1 wt % to 3.0 wt % of transition metal optionally comprising 0.1 wt % to 3.0 wt % of Zn.

Embodiment 6

The method of any of the above embodiments, wherein the conversion catalyst further comprises phosphorus supported on the conversion catalyst.

Embodiment 7

The method of any of the above embodiments, wherein at least one of the first catalyst system and the second catalyst system comprises at least 10 wt % of catalyst particles comprising a zeolite having MRE framework structure, the zeolite having a silicon to aluminum ratio of 10 to 100 and an Alpha value of at least 5, the first catalyst system and/or second catalyst system optionally further comprising 0.1 wt % to 3.0 wt % of a transition metal supported on the catalyst particles comprising the zeolite having MRE framework structure.

Embodiment 8

The method of any of the above embodiments, wherein at least one of the first catalyst system and the second catalyst system comprises at least 10 wt % of catalyst particles comprising a zeolite having MRE framework structure, MTW framework structure, TON framework structure, MTT framework structure, MFS framework structure or a combination thereof.

Embodiment 9

The method of any of the above embodiments, wherein at least one of the first catalyst system and the second catalyst system comprises at least 10 wt % of catalyst particles comprising a zeolite having a largest pore channel size corresponding to an 8-member ring.

Embodiment 10

The method of any of the above embodiments, a) wherein the oxygenates comprise methanol, the conversion catalyst comprising an average catalyst exposure time of 1 grams to 2000 grams of oxygenate per gram of catalyst; or b) wherein the average catalyst exposure time of the second catalyst is 50 grams to 180 grams of methanol per gram of catalyst; or c) an average catalyst exposure time of the first catalyst being different from an average catalyst exposure time of the second catalyst; or d) a combination thereof of a), b) and/or c).

Embodiment 11

The method of any of the above embodiments, wherein the first catalyst addition rate per day comprises at least about 10 vol % of the inventory volume, or at least 20 vol %; or wherein the composition of the second catalyst system differs from the composition of the first catalyst system by at least 10 wt %, or at least 30 wt %, or at least 50 wt %, or at least 70 wt %; or a combination thereof.

Embodiment 12

The method of any of the above embodiments, wherein the hydrocarbon fraction comprises olefins, or wherein the hydrocarbon fraction comprises a naphtha boiling range fraction, or a combination thereof.

Embodiment 13

A system for conversion of oxygenates to hydrocarbons, comprising: a first catalyst store comprising a first catalyst comprising a first zeolite framework structure; a second catalyst store comprising a second catalyst, the second catalyst comprising a second zeolite framework structure different from the first zeolite framework structure; and a reaction system comprising a reactor, a regenerator, and a reaction system internal catalyst store, the first catalyst store and the second catalyst store being in fluid communication with the reaction system, the reaction system further comprising an inventory volume of catalyst particles, the catalyst particles comprising the first catalyst and the second catalyst, the first catalyst in the internal catalyst store comprising less than 0.1 wt % coke, the second catalyst in the internal catalyst store comprising greater than 0.1 wt % coke, the reactor volume of the reactor optionally comprising the first catalyst, the second catalyst, and methanol.

Embodiment 14

The system of Embodiment 13, wherein the first catalyst comprises a zeolite having MFI framework structure, the zeolite having a silicon to aluminum ratio of 10 to 200 and an Alpha value of at least 5, the first catalyst optionally further comprising 0.1 wt % to 3.0 wt % of a transition metal supported on the catalyst; or wherein the second catalyst comprises a zeolite having MRE framework structure, the zeolite having a silicon to aluminum ratio of 10 to 100 and an Alpha value of at least 5, the second catalyst optionally further comprising 0.1 wt % to 3.0 wt % of a transition metal supported on the catalyst; or a combination thereof.

Embodiment 15

The system of Embodiment 13 or 14, wherein at least one of the first catalyst and the second catalyst comprises a zeolite having a largest pore channel size corresponding to an 8-member ring.

While the present invention has been described and illustrated by reference to particular embodiments, those of ordinary skill in the art will appreciate that the invention lends itself to variations not necessarily illustrated herein.

For this reason, then, reference should be made solely to the appended claims for purposes of determining the true scope of the present invention.

The invention claimed is:

1. A method for forming a hydrocarbon composition, comprising:
    introducing catalyst particles comprising a first catalyst system at a first catalyst addition rate per day into a reaction system comprising a reactor, the reaction system comprising an inventory volume of catalyst particles of a second catalyst system in the reactor, a composition of the second catalyst system being distinct from a composition of the first catalyst system by at least 10 wt %, the first catalyst addition rate per day comprising at least about 5 vol % of the inventory volume;
    exposing a feed comprising oxygenates to conversion catalyst in the reactor at conversion conditions to form a converted effluent comprising a hydrocarbon fraction, the conversion catalyst comprising at least a portion of the first catalyst system and at least a portion of the second catalyst system.

2. The method of claim 1, wherein the conversion catalyst in the reactor comprises a first catalyst having a first exposure time and a second catalyst having a second exposure time, a selectivity of the first catalyst for aromatics at the conversion conditions being at least 10 wt % greater than a selectivity of the second catalyst for aromatics at the conversion conditions.

3. The method of claim 1, wherein the second catalyst system comprises a first catalyst and a second catalyst.

4. The method of claim 3, further comprising regenerating at least a portion of the conversion catalyst exposed to the feed comprising oxygenates, the regenerated second catalyst comprising at least 0.1 wt % of coke.

5. The method of claim 3, wherein the regenerated first catalyst comprises 0.1 wt % or less of coke.

6. The method of claim 1, wherein at least one of the first catalyst system and the second catalyst system comprises at least 10 wt % of catalyst particles comprising a zeolite having MFI framework structure, the zeolite having a silicon to aluminum ratio of 10 to 200 and an Alpha value of at least 5, the first catalyst system and/or second catalyst system optionally further comprising 0.1 wt % to 3.0 wt % of a transition metal supported on the catalyst particles comprising the zeolite having MFI framework structure.

7. The method of claim 1, wherein the at least one of the first catalyst system and the second catalyst system further comprises 0.1 wt % to 3.0 wt % of transition metal, 0.1 wt % to 3.0 wt % of Zn, or a combination thereof.

8. The method of claim 1, wherein the conversion catalyst further comprises phosphorus supported on the conversion catalyst.

9. The method of claim 1, wherein the first catalyst system and/or the second catalyst system comprises at least 10 wt % of catalyst particles comprising a zeolite having MRE framework structure, the zeolite having a silicon to aluminum ratio of 10 to 100 and an Alpha value of at least 5, the first catalyst system and/or second catalyst system optionally further comprising 0.1 wt % to 3.0 wt % of a transition metal supported on the catalyst particles comprising the zeolite having MRE framework structure.

10. The method of claim 1, wherein the first catalyst system and/or the second catalyst system comprises at least 10 wt % of catalyst particles comprising a zeolite having MRE framework structure, MTW framework structure, TON framework structure, MTT framework structure, MFS framework structure or a combination thereof.

11. The method of claim 1, wherein the first catalyst system and/or the second catalyst system comprises at least 10 wt % of catalyst particles comprising a zeolite having a largest pore channel size corresponding to an 8-member ring.

12. The method of claim 1, wherein the oxygenates comprise methanol, the conversion catalyst comprising an average catalyst exposure time of 1 grams to 2000 grams of oxygenate per gram of catalyst.

13. The method of claim 12, wherein the conversion catalyst comprises a first catalyst and a second catalyst, an average catalyst exposure time of the first catalyst being different from an average catalyst exposure time of the second catalyst.

14. The method of claim 13, wherein the average catalyst exposure time of the second catalyst is 50 grams to 180 grams of methanol per gram of catalyst.

15. The method of claim 1, wherein exposing the feed comprising oxygenates to a conversion catalyst comprises exposing the feed comprising oxygenates to the conversion catalyst in a fluidized bed reactor, a moving bed reactor, a riser reactor, or a combination thereof.

16. The method of claim 1, wherein the first catalyst addition rate per day comprises at least about 10 vol % of the inventory volume.

17. The method of claim 1, wherein the composition of the second catalyst system differs from the composition of the first catalyst system by at least 30 wt %.

18. The method of claim 1, wherein the hydrocarbon fraction comprises olefins, or wherein the hydrocarbon fraction comprises a naphtha boiling range fraction, or a combination thereof.

19. A system for conversion of oxygenates to hydrocarbons, comprising:
    a first catalyst store comprising a first catalyst comprising a first zeolite framework structure;
    a second catalyst store comprising a second catalyst, the second catalyst comprising a second zeolite framework structure different from the first zeolite framework structure;
    a reaction system comprising a reactor, a regenerator, and a reaction system internal catalyst store, the first catalyst store and the second catalyst store being in fluid communication with the reaction system, the reaction system further comprising an inventory volume of catalyst particles in the reactor, the catalyst particles comprising the first catalyst and the second catalyst, the first catalyst in the internal catalyst store comprising less than 0.1 wt % coke, the second catalyst in the internal catalyst store comprising greater than 0.1 wt % coke.

20. The system of claim 19, wherein the first catalyst comprises a zeolite having MFI framework structure, the zeolite having a silicon to aluminum ratio of 10 to 200, an Alpha value of at least 5, and 0.1 wt % to 3.0 wt % of a transition metal supported on the catalyst.

21. The system of claim 19, wherein the second catalyst comprises a zeolite having MRE framework structure, the zeolite having a silicon to aluminum ratio of 10 to 100, an Alpha value of at least 5, and 0.1 wt % to 3.0 wt % of a transition metal supported on the catalyst.

22. The system of claim 19, wherein the second catalyst comprises a zeolite having a largest pore channel size corresponding to an 8-member ring.

23. The system of claim 19, wherein a reactor volume of the reactor comprises the first catalyst, the second catalyst, and methanol.

\* \* \* \* \*